(12) United States Patent
Sugar et al.

(10) Patent No.: US 12,070,217 B2
(45) Date of Patent: Aug. 27, 2024

(54) PRESSURE PROFILE MAGNETIC COMPRESSION ANASTOMOSIS DEVICES

(71) Applicant: G.I. Windows, Inc., Westwood, MA (US)

(72) Inventors: Peter F. Sugar, Charlestown, MA (US); Dane T. Seddon, Boston, MA (US)

(73) Assignee: G.I. Windows, Inc., Westwood, MA (US)

( * ) Notice: Subject to any disclaimer, the term of this patent is extended or adjusted under 35 U.S.C. 154(b) by 0 days.

(21) Appl. No.: 18/241,529

(22) Filed: Sep. 1, 2023

(65) Prior Publication Data
US 2024/0074759 A1 Mar. 7, 2024

Related U.S. Application Data

(60) Provisional application No. 63/403,181, filed on Sep. 1, 2022.

(51) Int. Cl.
*A61B 17/11* (2006.01)
*A61B 17/00* (2006.01)

(52) U.S. Cl.
CPC .... *A61B 17/1114* (2013.01); *A61B 17/00234* (2013.01); *A61B 2017/0034* (2013.01);
(Continued)

(58) Field of Classification Search
CPC .......... A61B 17/00234; A61B 17/1114; A61B 2017/0034; A61B 2017/00809;
(Continued)

(56) References Cited

U.S. PATENT DOCUMENTS

| 4,197,840 A | 4/1980 | Beck et al. |
| 4,538,130 A | 8/1985 | Gluckstern et al. |

(Continued)

FOREIGN PATENT DOCUMENTS

| CN | 105011985 A | 11/2015 |
| CN | 205379345 U | 7/2016 |

(Continued)

OTHER PUBLICATIONS

Author Unknown, "An Innovative Implant for the Creation of Anastomosis," PLIO, retrieved from the internet at: https://pliosurgical.com/, Jan. 19, 2024 (13 pages).

(Continued)

*Primary Examiner* — Mohamed G Gabr
(74) *Attorney, Agent, or Firm* — Nutter McClennen & Fish LLP

(57) ABSTRACT

Compression anastomosis devices having a plurality of distinct pressure profile zones on the surface of the device. The anastomosis devices may be comprised of a plurality of magnetic connecting members arranged in an annular geometry, e.g., a polygon or circle. The anastomosis device may also be a continuous, non-segmented magnet, or other compression anastomosis device. The compression anastomosis device is deployed into a body lumen, e.g., endoscopically and/or laparoscopically, at a target site. A second compression anastomosis device is placed at an adjacent target site in an adjacent lumen. The compression anastomosis devices are brought together and mate, e.g., magnetically, creating an anastomosis.

20 Claims, 31 Drawing Sheets

(52) U.S. Cl.
CPC .............. *A61B 2017/00809* (2013.01); *A61B 2017/00876* (2013.01); *A61B 2017/1107* (2013.01); *A61B 2017/1117* (2013.01); *A61B 2017/1132* (2013.01)

(58) Field of Classification Search
CPC .. A61B 2017/00876; A61B 2017/1107; A61B 2017/1117; A61B 2017/1132; A61B 2017/1139
See application file for complete search history.

(56) References Cited

U.S. PATENT DOCUMENTS

| | | |
|---|---|---|
| 5,300,910 A | 4/1994 | Unkelbach et al. |
| 5,320,629 A | 6/1994 | Noda et al. |
| 5,381,784 A | 1/1995 | Adair |
| 5,431,670 A | 7/1995 | Holmes |
| 5,595,562 A | 1/1997 | Grier |
| 5,690,656 A | 11/1997 | Cope et al. |
| 6,129,668 A | 10/2000 | Haynor et al. |
| 6,132,458 A | 10/2000 | Staehle et al. |
| 6,190,303 B1 | 2/2001 | Glenn et al. |
| 6,273,895 B1 | 8/2001 | Pinchuk et al. |
| 6,352,543 B1 | 3/2002 | Cole |
| 6,371,964 B1 | 4/2002 | Vargas et al. |
| 6,478,210 B2 | 11/2002 | Adams et al. |
| 6,537,284 B1 | 3/2003 | Inoue |
| 6,632,229 B1 | 10/2003 | Yamanouchi et al. |
| 6,652,540 B1 | 11/2003 | Cole et al. |
| 6,699,263 B2 | 3/2004 | Cope |
| 6,719,768 B1 | 4/2004 | Cole et al. |
| 6,802,847 B1 | 10/2004 | Carson et al. |
| 6,827,718 B2 | 12/2004 | Hutchins et al. |
| 6,932,827 B2 | 8/2005 | Cole |
| 7,282,057 B2 | 10/2007 | Surti et al. |
| 7,618,427 B2 | 11/2009 | Oritz et al. |
| 7,641,638 B2 | 1/2010 | Waxman et al. |
| 7,760,059 B2 | 7/2010 | Higuchi |
| 7,909,837 B2 | 3/2011 | Crews et al. |
| 8,043,290 B2 | 10/2011 | Harrison et al. |
| 8,118,821 B2 | 2/2012 | Mouw |
| 8,142,454 B2 * | 3/2012 | Harrison ............ A61B 17/8076 606/153 |
| 8,262,680 B2 | 9/2012 | Swain et al. |
| 8,439,915 B2 | 5/2013 | Harrison et al. |
| 8,506,516 B2 | 8/2013 | Kassab et al. |
| 8,518,062 B2 | 8/2013 | Cole et al. |
| 8,556,919 B2 | 10/2013 | Aguirre et al. |
| 8,603,121 B2 | 12/2013 | Surti et al. |
| 8,623,036 B2 | 1/2014 | Harrison et al. |
| 8,679,139 B2 | 3/2014 | Aguirre et al. |
| 8,685,046 B2 | 4/2014 | Viola |
| 8,728,105 B2 | 5/2014 | Aguirre |
| 8,794,243 B2 | 8/2014 | Deem et al. |
| 8,828,031 B2 | 9/2014 | Fox et al. |
| 8,828,032 B2 | 9/2014 | McWeeney et al. |
| 8,845,663 B2 | 9/2014 | Chmura |
| 8,864,781 B2 | 10/2014 | Surti et al. |
| 8,870,899 B2 | 10/2014 | Beisel et al. |
| 8,915,915 B2 | 12/2014 | Harrison et al. |
| 9,168,041 B2 | 10/2015 | Zaritsky et al. |
| 9,226,753 B2 | 1/2016 | Surti et al. |
| 9,320,524 B2 | 4/2016 | Gagner et al. |
| 9,421,015 B2 | 8/2016 | Gagner et al. |
| 9,456,820 B2 | 10/2016 | Gagner et al. |
| 9,492,173 B2 | 11/2016 | McWeeney et al. |
| 9,539,010 B2 | 1/2017 | Gagner et al. |
| 9,763,664 B2 | 9/2017 | Beisel et al. |
| 9,801,635 B2 | 10/2017 | Gagner et al. |
| 9,877,724 B2 | 1/2018 | Gagner et al. |
| 9,943,335 B2 | 4/2018 | Gittard et al. |
| 10,039,550 B2 | 8/2018 | Altman |
| 10,159,487 B2 | 12/2018 | Gagner et al. |
| 10,182,821 B2 | 1/2019 | Lukin et al. |
| 10,285,703 B2 | 5/2019 | Viola |
| 10,342,544 B2 | 7/2019 | Bakos et al. |
| 10,376,400 B2 | 8/2019 | McGuckin, Jr. |
| 10,448,954 B2 | 10/2019 | McWeeney et al. |
| 10,517,600 B2 | 12/2019 | Beisel et al. |
| 10,555,735 B2 | 2/2020 | Bakos et al. |
| 10,568,630 B2 | 2/2020 | Hernandez et al. |
| 10,595,869 B2 | 3/2020 | Beisel et al. |
| 10,624,643 B2 | 4/2020 | Hunt et al. |
| 10,624,644 B2 | 4/2020 | Bakos et al. |
| 10,631,865 B2 | 4/2020 | Bakos et al. |
| 10,667,817 B2 | 6/2020 | Gagner et al. |
| 10,682,143 B2 | 6/2020 | Hernandez et al. |
| 10,779,831 B2 | 9/2020 | Lukin et al. |
| 10,813,642 B2 | 10/2020 | Beisel et al. |
| 10,952,732 B2 | 3/2021 | Binmoeller et al. |
| 11,039,838 B2 | 6/2021 | Binmoeller et al. |
| 11,311,298 B2 | 4/2022 | Gagner et al. |
| 11,432,873 B2 | 9/2022 | Brown et al. |
| 2002/0055674 A1 | 5/2002 | Ben-Haim et al. |
| 2002/0143347 A1 * | 10/2002 | Cole .................... A61B 17/11 606/153 |
| 2003/0149422 A1 | 8/2003 | Muller |
| 2003/0176767 A1 | 9/2003 | Long et al. |
| 2004/0034377 A1 | 2/2004 | Sharkawy et al. |
| 2004/0059280 A1 | 3/2004 | Makower et al. |
| 2005/0020958 A1 | 1/2005 | Paolini et al. |
| 2005/0080439 A1 | 4/2005 | Carson et al. |
| 2005/0256503 A1 | 11/2005 | Hall |
| 2005/0277966 A1 | 12/2005 | Ewers et al. |
| 2005/0283235 A1 | 12/2005 | Kugler et al. |
| 2006/0036267 A1 | 2/2006 | Saadat et al. |
| 2006/0271107 A1 | 11/2006 | Harrison et al. |
| 2006/0282106 A1 | 12/2006 | Cole et al. |
| 2007/0106312 A1 | 5/2007 | Vargas et al. |
| 2007/0276378 A1 | 11/2007 | Harrison et al. |
| 2008/0051626 A1 | 2/2008 | Sato et al. |
| 2008/0086192 A1 | 4/2008 | WasDyke et al. |
| 2008/0114384 A1 | 5/2008 | Chang et al. |
| 2008/0183272 A1 | 7/2008 | Wood et al. |
| 2008/0200933 A1 | 8/2008 | Bakos et al. |
| 2008/0200934 A1 | 8/2008 | Fox |
| 2008/0208105 A1 | 8/2008 | Zelickson et al. |
| 2008/0208224 A1 | 8/2008 | Surti et al. |
| 2008/0243225 A1 | 10/2008 | Satasiya et al. |
| 2008/0262523 A1 | 10/2008 | Makower et al. |
| 2009/0048618 A1 | 2/2009 | Harrison et al. |
| 2009/0062824 A1 | 3/2009 | Berg et al. |
| 2009/0125042 A1 | 5/2009 | Mouw |
| 2009/0227828 A1 | 9/2009 | Swain et al. |
| 2010/0010508 A1 | 1/2010 | Takahashi et al. |
| 2010/0010610 A1 | 1/2010 | Grevious |
| 2010/0036399 A1 | 2/2010 | Viola |
| 2010/0056861 A1 | 3/2010 | Spivey |
| 2010/0099947 A1 | 4/2010 | Sato et al. |
| 2010/0179510 A1 | 7/2010 | Fox et al. |
| 2011/0009886 A1 | 1/2011 | Gagner et al. |
| 2011/0098731 A1 | 4/2011 | Whitbrook et al. |
| 2011/0118765 A1 | 5/2011 | Aguirre |
| 2011/0144560 A1 | 6/2011 | Gagner et al. |
| 2011/0160751 A1 | 6/2011 | Granja Filho |
| 2011/0160752 A1 | 6/2011 | Aguirre |
| 2011/0295055 A1 | 12/2011 | Albrecht et al. |
| 2011/0295285 A1 | 12/2011 | Mcweeney et al. |
| 2012/0022572 A1 | 1/2012 | Braun et al. |
| 2012/0197062 A1 | 8/2012 | Requarth |
| 2012/0238796 A1 | 9/2012 | Conlon |
| 2012/0259350 A1 | 10/2012 | Gagner et al. |
| 2012/0330330 A1 | 12/2012 | Gagner et al. |
| 2013/0138126 A1 | 5/2013 | Gagner et al. |
| 2013/0150873 A1 | 6/2013 | Gagner et al. |
| 2013/0253548 A1 | 9/2013 | Harrison et al. |
| 2013/0253550 A1 | 9/2013 | Beisel et al. |
| 2013/0325042 A1 | 12/2013 | Fabian et al. |
| 2014/0018824 A1 | 1/2014 | Julian et al. |
| 2014/0019468 A1 | 1/2014 | Federoff et al. |
| 2014/0066709 A1 | 3/2014 | Mirza et al. |
| 2014/0188246 A1 | 7/2014 | Aronson et al. |
| 2014/0194689 A1 | 7/2014 | Carrillo, Jr. et al. |
| 2014/0236064 A1 | 8/2014 | Binmoeller et al. |

(56) References Cited

U.S. PATENT DOCUMENTS

| | | |
|---|---|---|
| 2014/0243592 A1 | 8/2014 | Kato et al. |
| 2014/0277342 A1 | 9/2014 | Roeder et al. |
| 2014/0303657 A1 | 10/2014 | Kim et al. |
| 2014/0309669 A1 | 10/2014 | Fabian et al. |
| 2014/0309670 A1 | 10/2014 | Bakos et al. |
| 2014/0343583 A1 | 11/2014 | McWeeney et al. |
| 2014/0379065 A1 | 12/2014 | Johnson et al. |
| 2015/0057687 A1 | 2/2015 | Gittard et al. |
| 2015/0164508 A1 | 6/2015 | Hernandez et al. |
| 2015/0182224 A1 | 7/2015 | Altman |
| 2016/0022266 A1* | 1/2016 | Lukin .............. A61B 17/1114 606/154 |
| 2016/0235442 A1 | 8/2016 | Palese et al. |
| 2016/0262761 A1 | 9/2016 | Beisel et al. |
| 2016/0287257 A1 | 10/2016 | Fabian et al. |
| 2016/0324523 A1 | 11/2016 | Lukin et al. |
| 2016/0367236 A1 | 12/2016 | Leeflang et al. |
| 2016/0374683 A1 | 12/2016 | Gagner et al. |
| 2017/0035425 A1 | 2/2017 | Fegelman et al. |
| 2017/0265866 A1 | 9/2017 | Ryou et al. |
| 2018/0028186 A1 | 2/2018 | Yamanouchi |
| 2018/0028187 A1 | 2/2018 | Gagner et al. |
| 2018/0193061 A1 | 7/2018 | Gittard et al. |
| 2018/0214149 A1 | 8/2018 | Hunt et al. |
| 2018/0214150 A1 | 8/2018 | Bakos et al. |
| 2018/0214152 A1 | 8/2018 | Bakos et al. |
| 2018/0263625 A1 | 9/2018 | Lukin et al. |
| 2018/0296218 A1 | 10/2018 | Binmoeller et al. |
| 2018/0361127 A1 | 12/2018 | Gray et al. |
| 2019/0133587 A1 | 5/2019 | Gagner et al. |
| 2019/0133678 A1 | 5/2019 | Pate et al. |
| 2019/0183507 A1 | 6/2019 | Baillargeon |
| 2019/0216460 A1 | 7/2019 | Kopelman |
| 2019/0261998 A1 | 8/2019 | Altman et al. |
| 2019/0274687 A1 | 9/2019 | Wang et al. |
| 2019/0328392 A1 | 10/2019 | Sharma |
| 2020/0008834 A1 | 1/2020 | Cauche et al. |
| 2020/0129283 A1 | 4/2020 | Swensgard et al. |
| 2020/0138438 A1 | 5/2020 | Harrison et al. |
| 2020/0170776 A1 | 6/2020 | Folan |
| 2020/0187947 A1 | 6/2020 | Hernandez et al. |
| 2020/0222049 A1 | 7/2020 | McWeeney et al. |
| 2020/0229968 A1 | 7/2020 | Galloway |
| 2020/0246009 A1 | 8/2020 | Gagner et al. |
| 2020/0323530 A1 | 10/2020 | Sharma |
| 2021/0100554 A1 | 4/2021 | Seddon et al. |
| 2021/0161532 A1 | 6/2021 | Beisel et al. |
| 2021/0169485 A1 | 6/2021 | Beisel et al. |
| 2021/0169486 A1 | 6/2021 | Gagner et al. |
| 2021/0244414 A1 | 8/2021 | Lukin et al. |
| 2022/0087678 A1 | 3/2022 | Gagner et al. |
| 2022/0104956 A1 | 4/2022 | Pham et al. |
| 2022/0257252 A1 | 8/2022 | Todd et al. |
| 2023/0165585 A1 | 6/2023 | McWeeney et al. |
| 2023/0172608 A1 | 6/2023 | Lukin et al. |
| 2023/0190269 A1 | 6/2023 | Tinkham et al. |
| 2023/0255624 A1 | 8/2023 | Wallace et al. |
| 2023/0389923 A1 | 12/2023 | Tinkham et al. |
| 2023/0389924 A1 | 12/2023 | Seddon et al. |
| 2024/0041460 A1 | 2/2024 | Seddon |
| 2024/0041461 A1 | 2/2024 | Tinkham et al. |
| 2024/0065694 A1 | 2/2024 | Seddon |
| 2024/0074751 A1 | 3/2024 | Tinkham et al. |
| 2024/0074755 A1 | 3/2024 | Mann et al. |

FOREIGN PATENT DOCUMENTS

| | | |
|---|---|---|
| DE | 3011742 A1 | 10/1981 |
| EP | 1894514 A2 | 3/2008 |
| EP | 1493391 B1 | 12/2009 |
| EP | 2207488 B1 | 9/2012 |
| EP | 2538852 A1 | 1/2013 |
| EP | 3267905 A1 | 1/2018 |
| EP | 2260752 B1 | 3/2018 |
| EP | 3573542 A1 | 12/2019 |
| EP | 3487418 A4 | 4/2020 |
| EP | 4115949 A1 | 1/2023 |
| JP | 2003530916 A | 10/2003 |
| JP | 2006271832 A | 10/2006 |
| JP | 2008508939 A | 3/2008 |
| JP | 2011500159 A | 1/2011 |
| JP | 2015139592 A | 8/2015 |
| JP | 2017/521223 A | 8/2017 |
| JP | 202198077 A | 7/2021 |
| KR | 20150102567 A | 9/2015 |
| RU | 2018266 C1 | 8/1994 |
| SU | 1708313 A1 | 1/1992 |
| SU | 1725851 A1 | 4/1992 |
| WO | 01/087398 A2 | 11/2001 |
| WO | 01/93920 A2 | 12/2001 |
| WO | 2009048954 A1 | 4/2009 |
| WO | 2011085006 A2 | 7/2011 |
| WO | 2011/103400 A1 | 8/2011 |
| WO | 2013009886 A1 | 1/2013 |
| WO | 2013/176993 A1 | 11/2013 |
| WO | 2014055193 A1 | 4/2014 |
| WO | 2016082481 A1 | 6/2016 |
| WO | 2016/145414 A1 | 9/2016 |
| WO | 2018022180 A1 | 2/2018 |
| WO | 2018/138632 A1 | 8/2018 |
| WO | 2019077218 A1 | 4/2019 |
| WO | 2019232526 A1 | 12/2019 |
| WO | 2019232527 A1 | 12/2019 |
| WO | 2020/196336 A1 | 10/2020 |
| WO | 2021/203910 A1 | 10/2021 |
| WO | 2021/207821 A1 | 10/2021 |
| WO | 2022/061117 A1 | 3/2022 |
| WO | 2022/132351 A1 | 6/2022 |
| WO | 2022/171349 A1 | 8/2022 |

OTHER PUBLICATIONS

European Patent Office, Communication pursuant to Article 94(3) EPC for Application No. 19810895.3, dated Feb. 13, 2023 (3 pages).
Extended European Search Report of the European Patent Office, Application No. 19810895.3, dated Feb. 7, 2022, 10 pages.
Gagner, M., "Duodeno-lleal Anastomosis with Self- Assembling Magnets: Initial Concepts and Basis of This Operation", Obesity Surgery 32, 932-933 (2022).
International Search Report and Written Opinion of the International Searching Authority, Application No. PCT/US2019035202, mailed Aug. 8, 2019, 6 pages.
International Search Report and Written Opinion of the International Searching Authority, Application No. PCT/US2022/25343, mailed Jul. 18, 2022, 14 pages.
International Search Report and Written Opinion of the International Searching Authority, Application No. PCT/US2022/25353, mailed Jun. 30, 2022, 12 pages.
International Search Report and Written Opinion of the International Searching Authority, for Application No. PCT/US2011/020229, with a date of mailing of Jun. 21, 2013, 6 pages.
International Search Report and Written Opinion of the International Searching Authority, for Application No. PCT/US2013/041641, dated Oct. 18, 2013, 4 pages.
International Search Report and Written Opinion of the International Searching Authority, for Application No. PCT/US2015/041498 dated Nov. 17, 2015, 17 pages.
International Search Report and Written Opinion of the International Searching Authority, for Application PCT/US2016/022209, dated May 30, 2016.
International Search Report and Written Opinion of the International Searching Authority, for Application PCT/US22/25338, dated Aug. 19, 2022, 14 pages.
International Search Report and Written Opinion of the International Searching Authority, for Application PCT/US23/29416, dated Dec. 7, 2023, 9 pages.
International Search Report and Written Opinion of the International Searching Authority, for Application PCT/US23/29432, dated Nov. 14, 2023, 7 pages.

(56) References Cited

OTHER PUBLICATIONS

International Search Report and Written Opinion issued for Application No. PCT/US2016/031547 dated Oct. 18, 2016, 18 pages.
Invitation to Pay Additional Fees and, Where Applicable, Protest Fee, from the International Search Authority, Application No. PCT/US2022/025338, mailed Jun. 23, 2022, 2 pages.
Invitation to Pay Additional Fees and, Where Applicable, Protest Fee, from the International Search Authority, Application No. PCT/US2022/025370, mailed Jun. 24, 2022, 3 pages.
Japanese Office Action for Japanese Patent Application No. 2021-034336 dated Dec. 17, 2021, 3 pages.
Japanese Penultimate Office Action for Japanese Patent Application No. 2021-034336 dated Aug. 1, 2022, 9 pages.
Japanese Office Action, Notice of Reasons for Refusal, Japanese Patent Application No. 2020-567134 dated Feb. 21, 2023.
Japanese Search Report, Japanese Application No. 2020-567134, dated Feb. 13, 2023, 28 pages.
Supplementary Partial European Search Report for Application No. EP 13793804.9 dated Jan. 15, 2016, 9 pages.
International Search Report and Written Opinion of the International Searching Authority, for Application PCT/2023/031863, dated Jan. 22, 2024, 8 pages.
International Search Report and Written Opinion of the International Searching Authority, for Application PCT/US2023/031861, dated Feb. 2, 2024, 9 pages.
International Search Report and Written Opinion of the International Searching Authority, for Application PCT/US2023/035976, dated Feb. 2, 2024, 11 pages.
Jamshidi, et al., "Magnamosis: magnetic compression anastomosis with comparison to suture and staple. Techniques," Journal of Pediatric Surgery, vol. 4, Issue 1, pp. 222-228. Jan. 20, 2009 (Jan. 20, 2009). [Retrieved on. May 12, 2023]. Retrieved from the Internet: <URL: https://dotorg/10.1016/j.jpedsurg.2008.10.044>. entire document.

* cited by examiner (A)

(B)

(A)

(B)

(C)

PRESSURE PROFILE MAGNETIC COMPRESSION ANASTOMOSIS DEVICES

CROSS-REFERENCE TO RELATED APPLICATION(S)

This patent application claims the benefit of U.S. Provisional Patent Application No. 63/403,181 entitled MAGNETIC ANASTOMOSIS DEVICES WITH VARYING MAGNETIC FORCE AT A DISTANCE filed Sep. 1, 2022, which is hereby incorporated herein by reference in its entirety.

FIELD OF INVENTION

The invention relates to deployable magnetic compression devices, and, more particularly, to systems, devices, and methods for the delivery, deployment, and positioning of magnetic compression devices at a desired site so as to improve the accuracy of anastomoses creation between tissues, organs, or the like.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency. Furthermore, placement of the magnets or couplings can be imprecise, which can lead to anastomosis formation in locations that is undesirable or inaccurate.

Tissues of different thicknesses require different pressures to puncture the tissues and/or bring magnetic anastomosis devices close enough together to mate. Sharp pressure profiles may cause abrupt transitions between healthy and necrotic tissues, which can cause poor sealing of the anastomosis.

Thus, there still remains a clinical need for reliable devices and minimally invasive procedures that facilitate compression anastomosis formation between tissues in the human body in as few steps as possible.

SUMMARY

In accordance with one embodiment, a magnetic compression anastomosis device comprises at least one magnetic member that forms an annular shape including a tissue-engaging surface comprising a plurality of distinct pressure profile zones selected from the group consisting of a cutting zone, a fast release zone, a tissue fusion zone, a relief zone, and a securing zone.

In various alternative embodiments, the relief zone is capable of generating pressure between around 0 psi to around 25 psi on body tissues; the tissue fusion zone is capable of generating between around 25 psi to around 250 psi on body tissues; the fast release zone is capable of generating between around 250 psi to around 40,000 psi on body tissues; and the cutting zone is capable of generating between around 40,000 psi to around 75,000 psi on body tissues. The plurality of distinct pressure profile zones may include an inner cutting zone; a fast response zone adjacent to the inner cutting zone; a tissue fusion zone adjacent to the fast response zone; and a relief zone adjacent to the tissue fusion zone. The securing zone may include a knurled or cross-hatched geometric profile. A geometric profile of at least one of the distinct pressure profile zones may be non-uniform and non-linear. The cutting zone may include an angled cutting pressure profile. The annular shape may be a polygon or a circle. The at least one magnetic member may include a plurality of magnetic members that assemble into the annular shape or may include a unitary magnetic member forming the annular shape.

In additional embodiments, a system may include first and second magnetic compression anastomosis devices of the types described with the second magnetic compression anastomosis device configured to engage with the first magnetic compression anastomosis device. The first and second devices may have the same pressure profile configurations or may have different but complementary pressure profile configurations.

Additional embodiments may be disclosed and claimed.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

It should be noted that the foregoing figures and the elements depicted therein are not necessarily drawn to consistent scale or to any scale. Unless the context otherwise suggests, like elements are indicated by like numerals. The drawings are primarily for illustrative purposes and are not intended to limit the scope of the inventive subject matter described herein.

DESCRIPTION OF ILLUSTRATIVE EMBODIMENTS

Various embodiments of the invention comprise compression anastomosis devices having varying geometric profiles across the surface of the device. The anastomosis devices may be comprised of a plurality of magnetic connecting members arranged in an annular geometry, e.g., a polygon or circle. The anastomosis device may also be a continuous, non-segmented magnet, or other compression anastomosis device. The compression anastomosis device is deployed into a body lumen, e.g., endoscopically and/or laparoscopically, at a target site. A second compression anastomosis device is placed at an adjacent target site in an adjacent lumen. The compression anastomosis devices are brought together and mate, e.g., magnetically, creating an anastomosis.

The tissue-engaging face of the compression anastomosis device has a varying geometric profile across the surface of the device to allow for varying pressure application on the tissue of the anastomosis. For example, the outer diameter of the device may have a lower pressure profile in order to allow for a smooth transition between healthy and necrotic tissue, while the inner diameter has a higher pressure profile to perforate tissue. This allows for the creation of more robust anastomoses and greater patient success.

Figure 22:
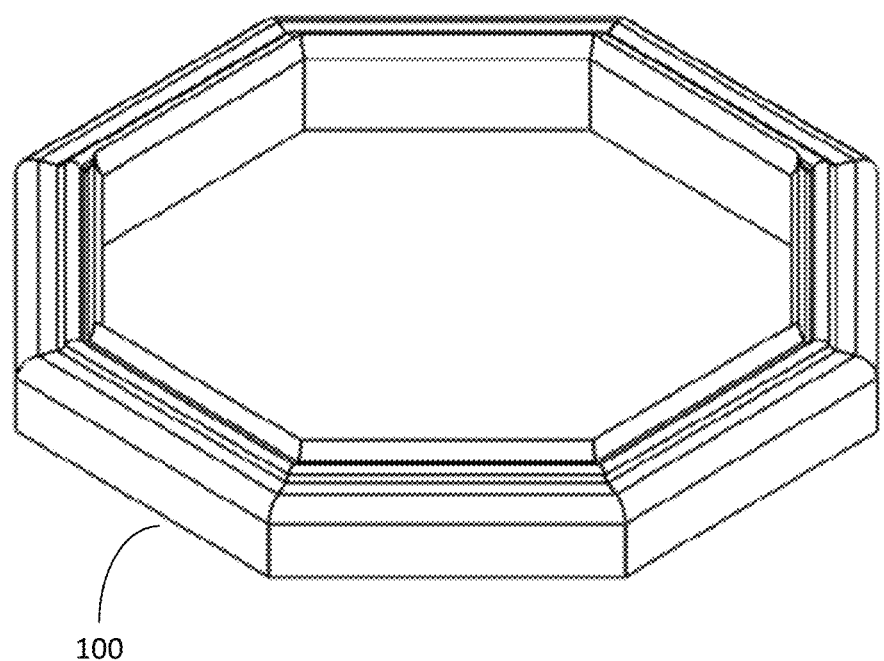
FIG. 22 schematically shows a compression anastomosis device having a varied pressure profile.

An embodiment of a varied pressure profile compression anastomosis device 100 is shown in FIG. 22. One or more faces of the compression anastomosis device has a varying geometric profile across the surface of the device, each profile capable of applying a different pressure on the tissue site.

Figure 23:
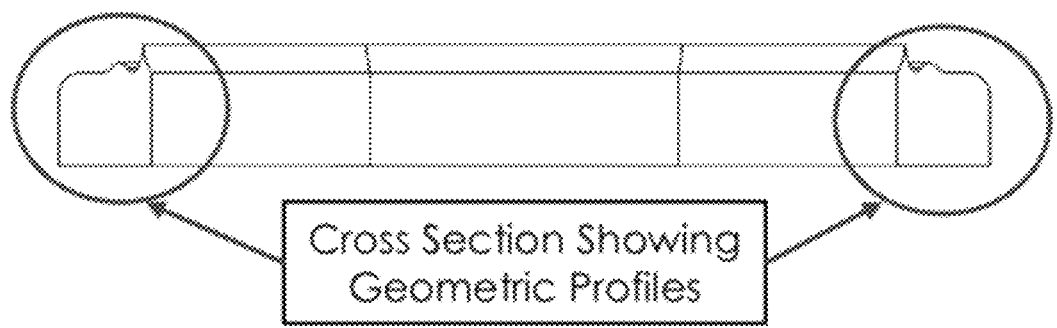
FIG. 23 schematically shows a cross section of a compression anastomosis device having a varying geometric profile.

As is shown in FIG. 23, each compression anastomosis device may have a varying geometric profile across the surface of the device comprising one or more profile zones. The profile zones may include, but are not limited to, the following:
  A relief profile capable of applying 0-25 psi on the tissue site. This profile gradually increases the pressure along the profile to allow for a smooth transition between healthy and necrotic tissue.
  A tissue fusion profile capable of applying 25-250 psi on the tissue site. This profile applies the required pressure to prevent interstitial fluid exchange across the compression anastomosis device and causes the tissue to necrose and form a collagenic seal.
  A fast release profile capable of applying 250-40,000 psi on the tissue site. This profile applies the required pressure to release the anastomosis device at the boundary line where the pressure is at its peak.
  A cutting profile capable of applying 40,000-75,000 psi on the tissue site. This profile applies the required pressure to perforate one or more tissue segments.

Figure 24:
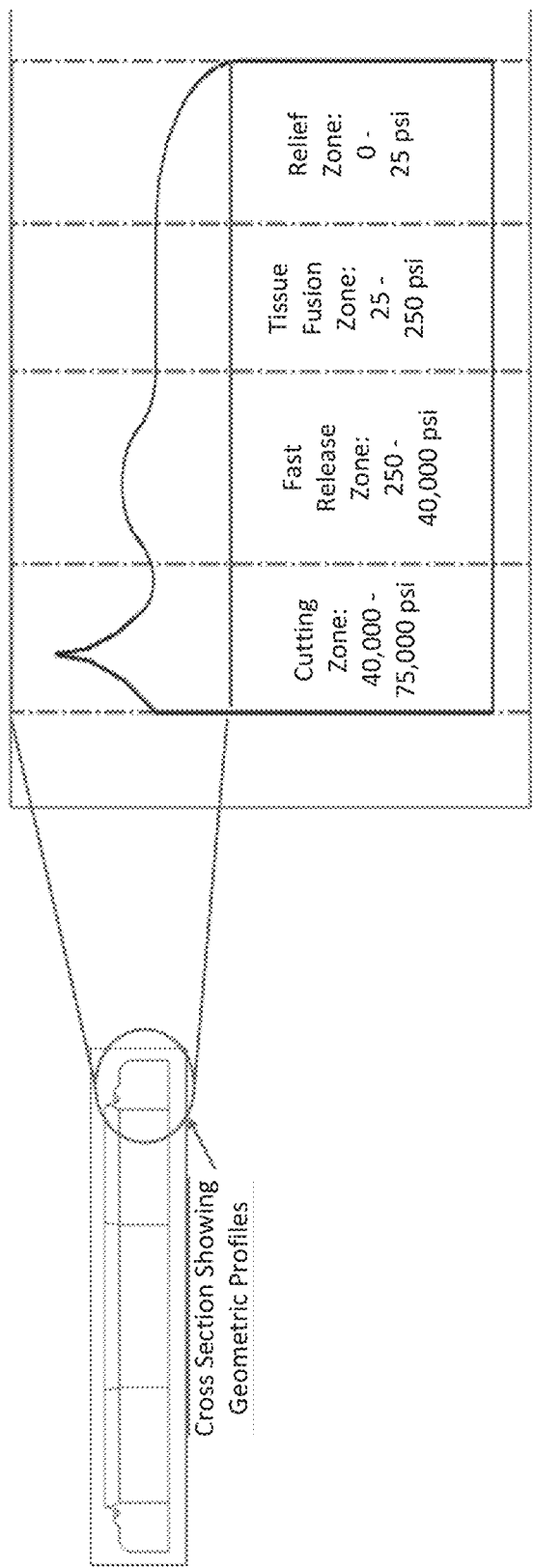
FIG. 24 schematically shows a cross section of various geometric pressure profiles.

FIG. 24 schematically shows a cross-section of a varied geometric profile on a compression anastomosis device. The geometric profile may include but is not limited to what is depicted in FIG. 24. The force and area of the pressure profile zone dictate which of the four zones the geometric profile falls under. Geometric profile zones may include, but are not limited to, a relief zone (0-25 psi), a tissue fusion zone (25-250 psi), a fast release zone (250-40,000 psi), and/or a cutting zone (40,000-75,000 psi). For a compression anastomosis device, the maximum available force in the system in conjunction with the geometric profile dictates the pressure.

Figure 25:
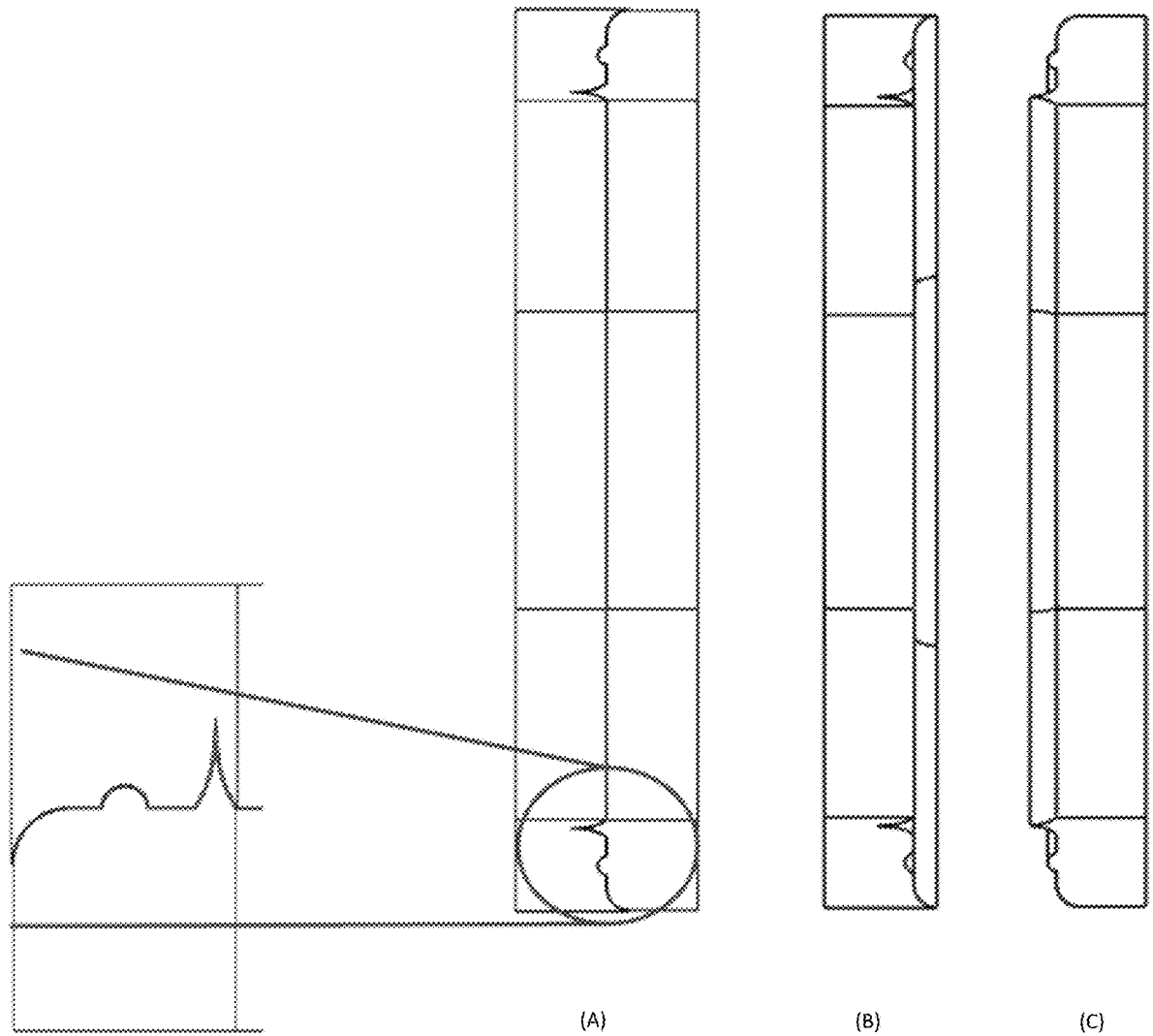
FIG. 25 schematically shows various reciprocating pressure profiles of two compression anastomosis devices.

FIGS. 25(A)-25(C) schematically show various reciprocating pressure profiles in two compression anastomosis devices. As shown in FIG. 25(A), one compression anastomosis device contains a varying geometric pressure profiles across the surface of the device and a second compression anastomosis device has a reciprocating geometric profile. This allows for the two anastomosis devices to mate with each other and create a compression anastomosis. The gap between the mating profiles may vary based on the geometry or the mating intention. The assembly of two mated compression anastomosis devices helps trap tissue in between its features to reduce slippage of the tissue. When mating the two reciprocating compression anastomosis devices, the varying geometric profile across the surface of the device allows the two devices to self-located and mate, creating an anastomosis.

Figure 26:
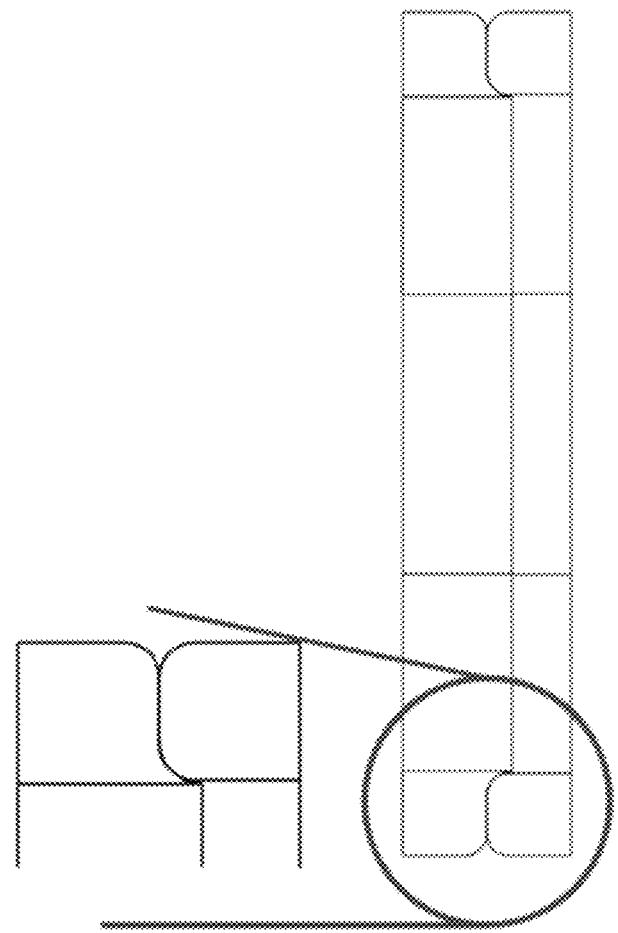
FIG. 26 schematically shows a reciprocating geometric profile of two compression anastomosis devices.

FIG. 26 schematically shows a reciprocating geometric profile between two compression anastomosis devices. Two reciprocating devices mate across tissues in adjacent body lumens, overlapping their geometries to facilitate otomy creation. As shown in FIG. 26, the cutting profile of the left anastomosis device overlays with the inner diameter of the right magnet, allowing an otomy to be created once a certain compression distance is achieved.

Figure 27:
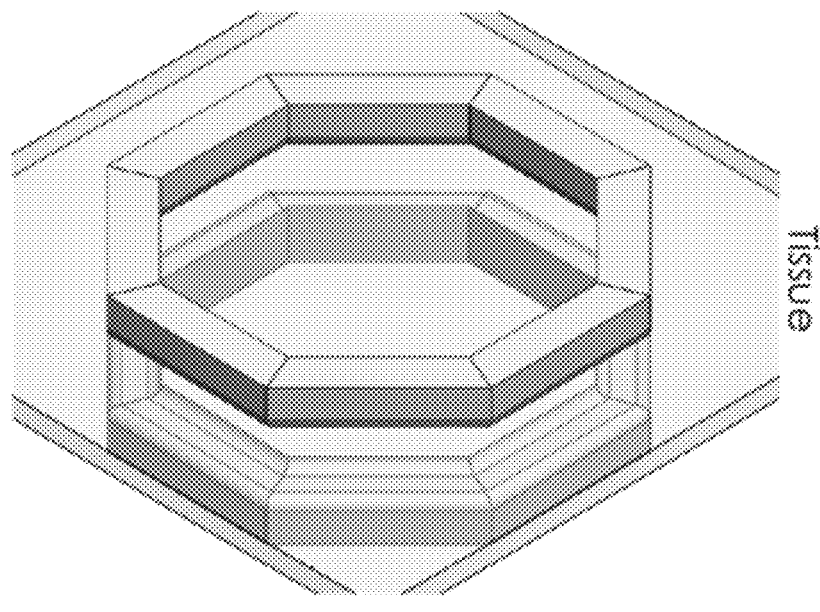
FIG. 27 schematically shows overlapping geometries of two compression anastomosis devices across tissue segments.
Figure 27:
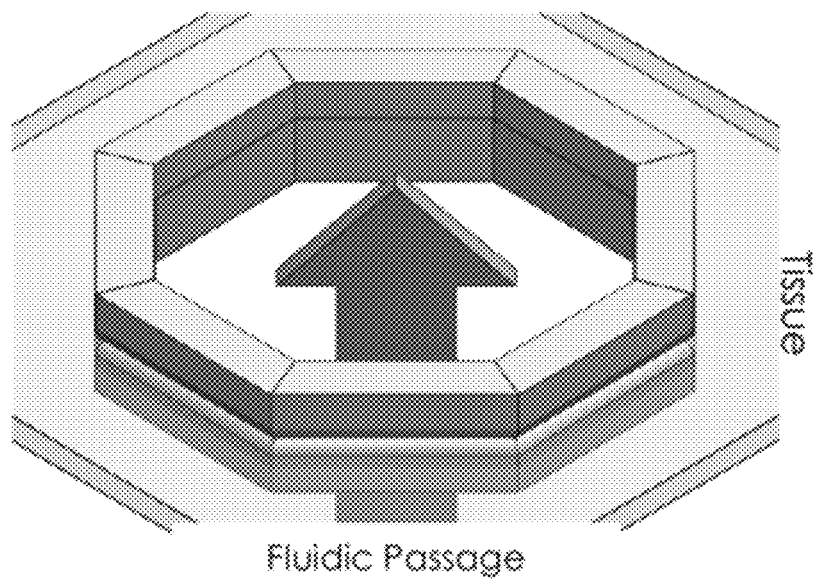

FIGS. 27(A)-27(B) schematically show two mating compression anastomosis devices with tissue in between the devices. The overlapping geometries of the compression anastomosis devices causes immediate release of the tissue within the inner diameter of the devices, allowing for immediate nutrient and fluid passage. This is done in conjunction with forming a sealed anastomosis.

Figure 28:
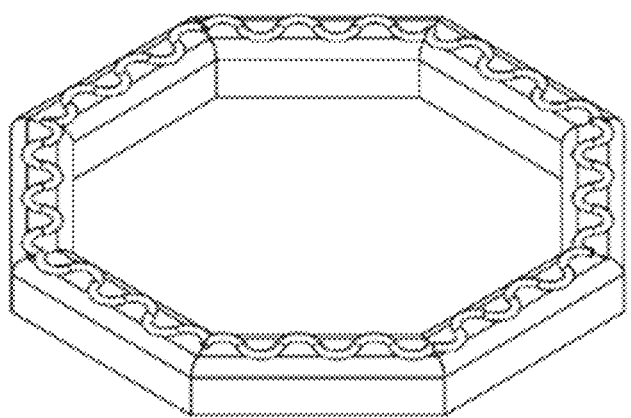
FIG. 28 schematically shows a compression anastomosis device with a non-uniform/non-linear geometry.

FIG. 28 schematically shows a non-limiting example of a compression anastomosis device comprising a non-uniform/non-linear pattern along the face of the device. This non-uniform pattern may contain one or more of the above-identified pressure profile zones. The shape and size of the non-uniform/non-linear pattern are bound by the pressure profile zones.

Figure 29:
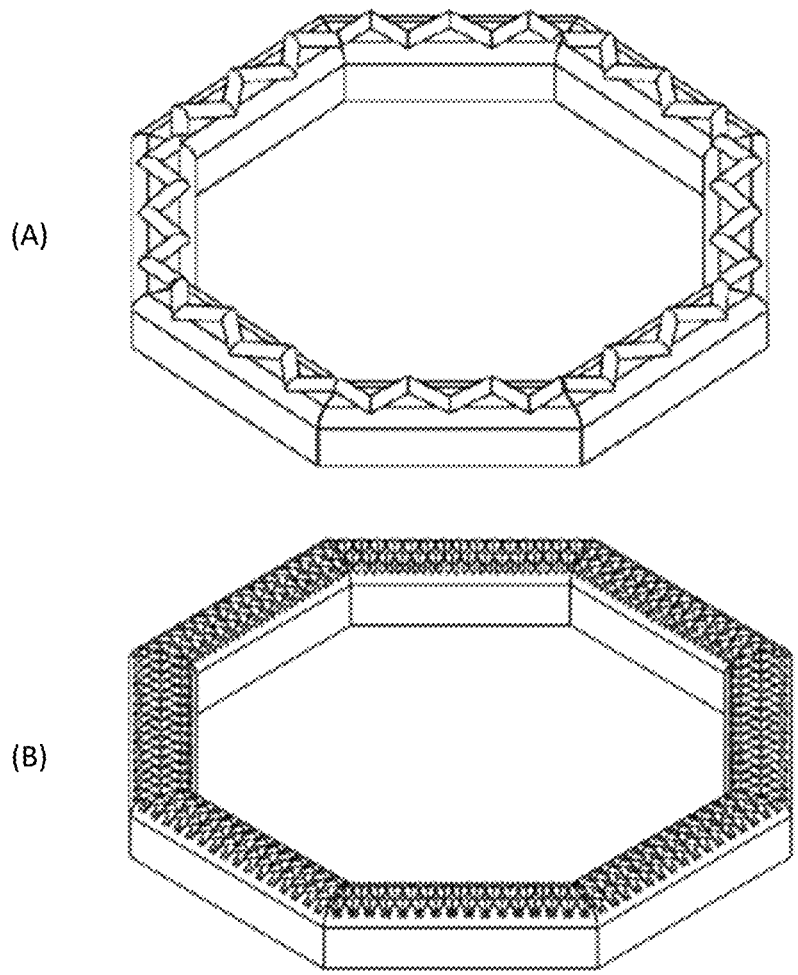
FIG. 29 schematically shows compression anastomosis devices with a knurled and cross-hatched pattern.

FIGS. 29(A)-29(B) schematically show non-limiting examples of compression anastomosis devices comprising a knurled pattern (FIG. 29(A)), and a cross-hatched pattern (FIG. 29(B)). These patterns, and others not depicted, help secure the tissue and prevent slippage when the compression anastomosis device is secured to the anastomosis site.

Figure 30:
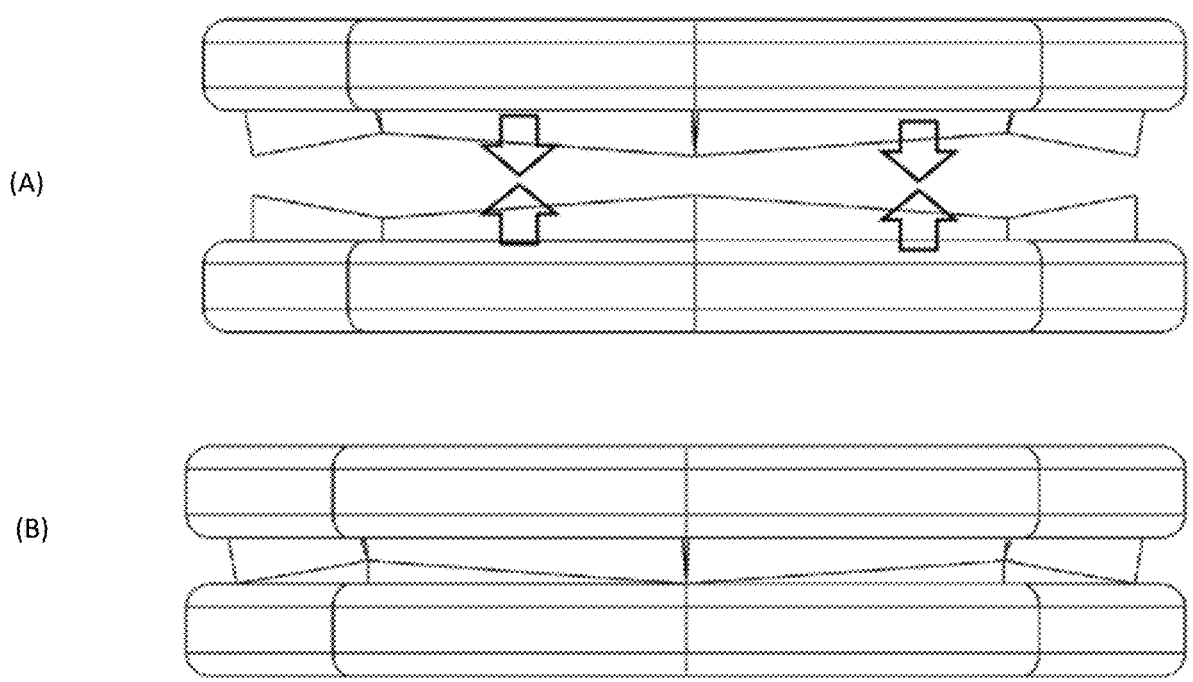
FIG. 30 schematically shows compression anastomosis devices with a cutting pressure profile.

FIGS. 30(A)-30(B) schematically show a compression anastomosis device comprising an angled cutting pressure profile on the face of the device. As two compression anastomosis devices mate (FIG. 30(A)), the cutting profiles overlap (FIG. 30(B)) causing the tissue to shear and break away, allowing for immediate nutrient and fluid passage through the anastomosis.

Figure 31:
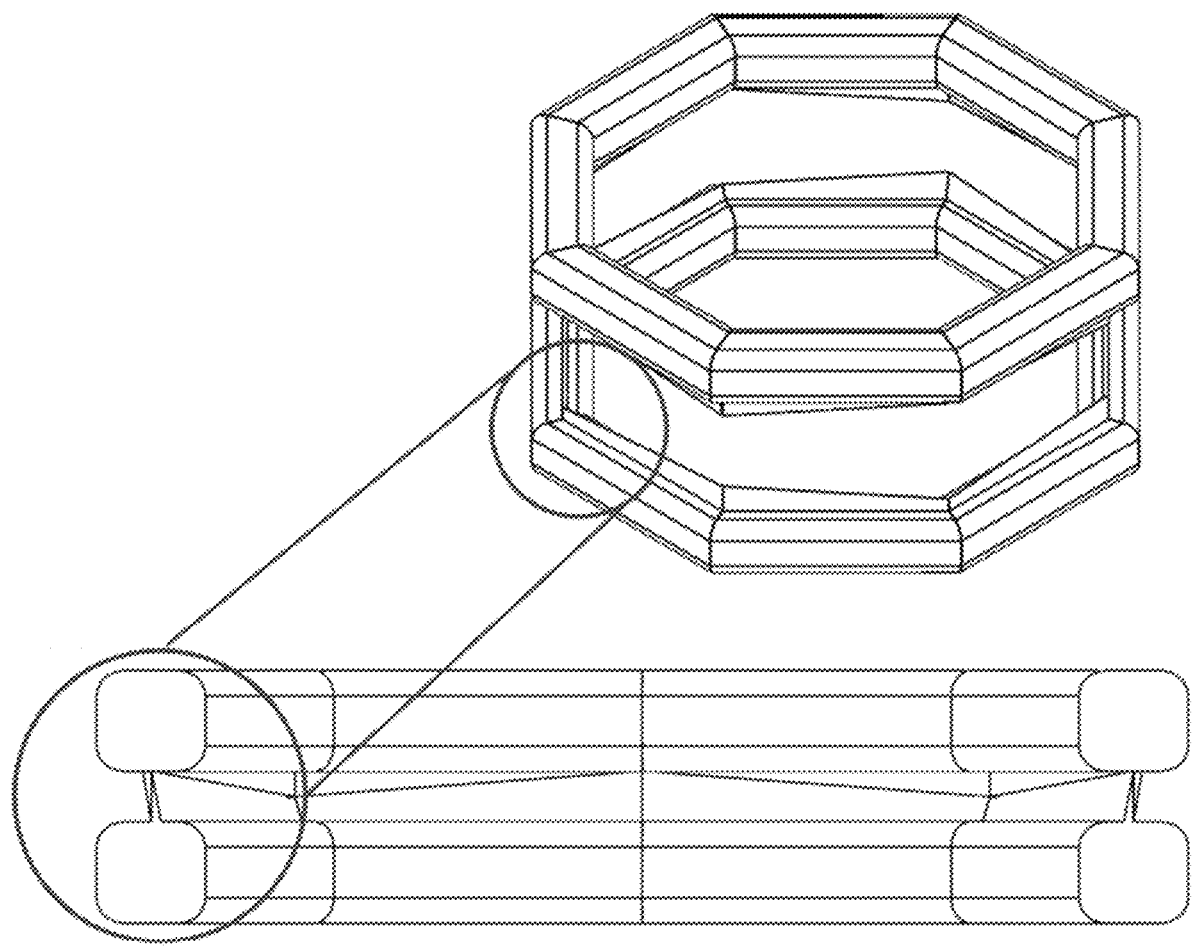
FIG. 31 schematically shows a close-up view of mated compression anastomosis devices.

FIG. 31 schematically shows a close-up view of mated compression anastomosis devices. The devices have reciprocating geometries, allowing for the angled cutting pressure profiles to interlock. Design features include, but are not limited to, tapered cutting profiles allowing the devices to overlap. Overlapping the geometries of the compression anastomosis devices allows for shearing of the tissue and immediate nutrient and fluid passage through the created anastomosis.

Figure 32:
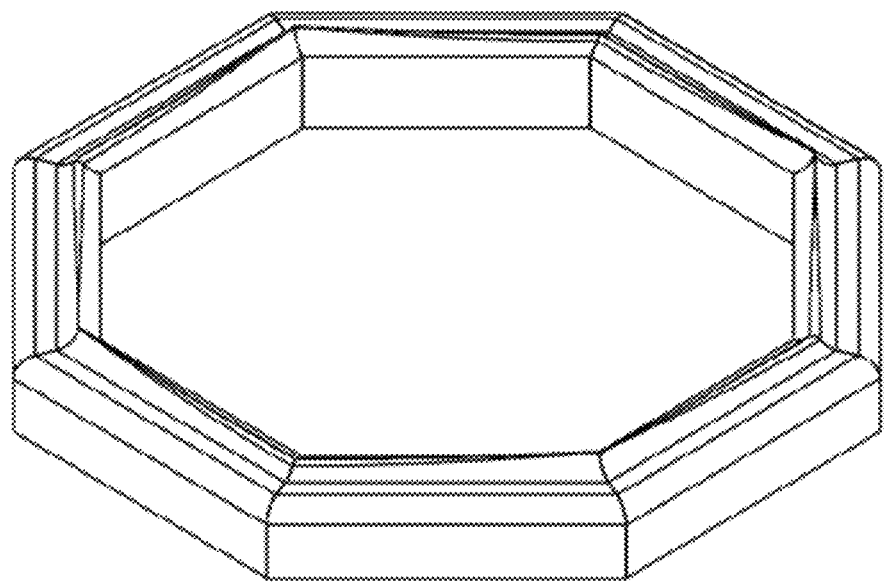
FIG. 32 schematically shows a compression anastomosis device having one or more alternating pressure profile zones.

FIG. 32 schematically shows a compression anastomosis device comprising one or more alternating pressure profile zones.

Figure 33:
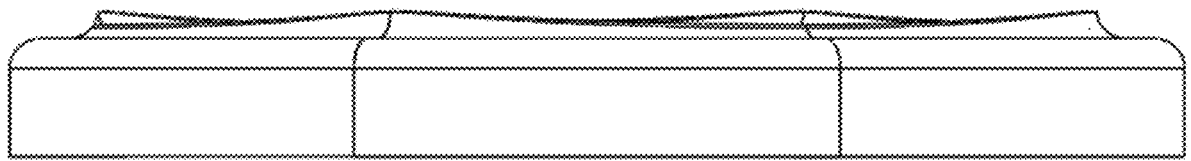
FIG. 33 schematically shows a compression anastomosis device having two or more alternating pressure profile zones.

FIG. 33 depicts a compression anastomosis device comprising two or more pressure profile zones with one geometric shape. These configurations allow the compression anastomosis device to provide one or more functions such as, but not limited to, relief, tissue fusion, fast release, and/or cutting. This may include, but is not limited to, the profile zones shown.

Figure 34:
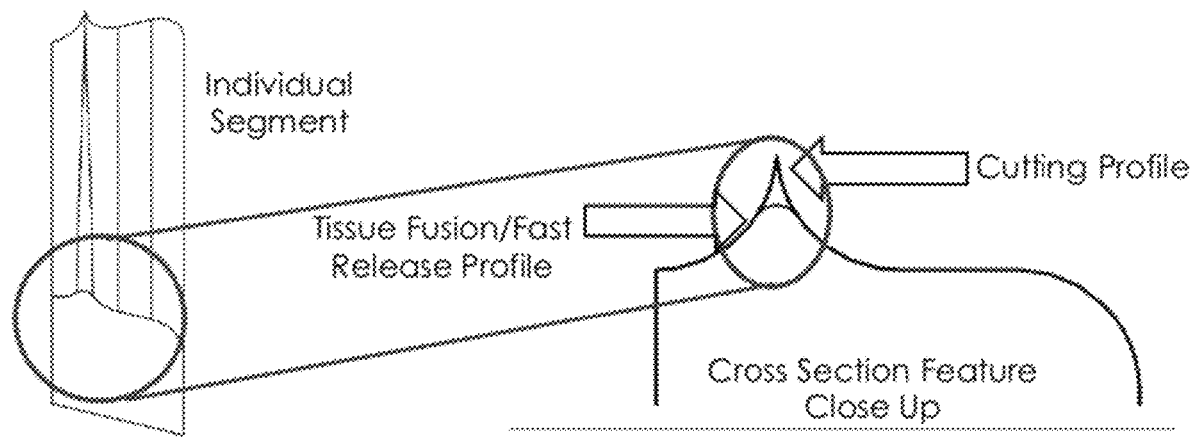
FIG. 34 schematically shows a cross-section of a compression anastomosis device having a varying geometric profile.

FIG. 34 schematically shows a cross-section of a compression anastomosis device comprising a cutting profile, tissue fusion, and fast release profile. The cutting pressure profile gradually smooths into a tissue fusion and/or fast release profile. This allows the compression anastomosis devices to puncture through the tissue segments, driving the compression anastomosis devices closer to one another to create an anastomosis.

Figure 35:
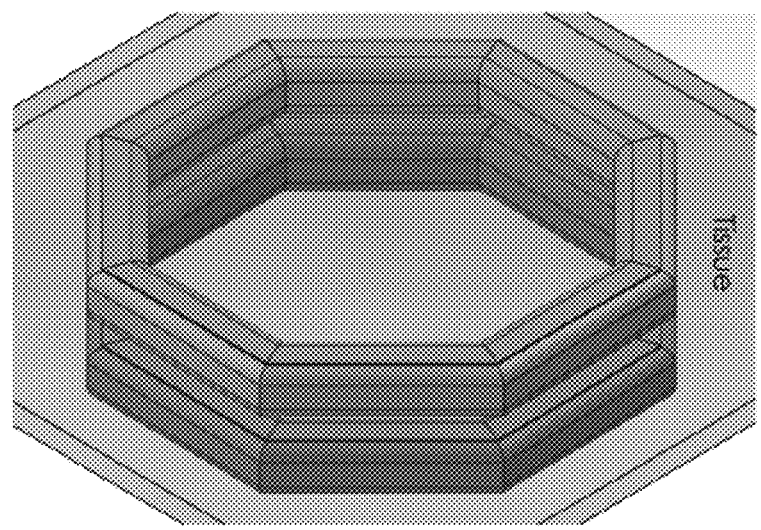
FIG. 35 schematically shows a compression anastomosis system having an insulating jacket.
Figure 35:
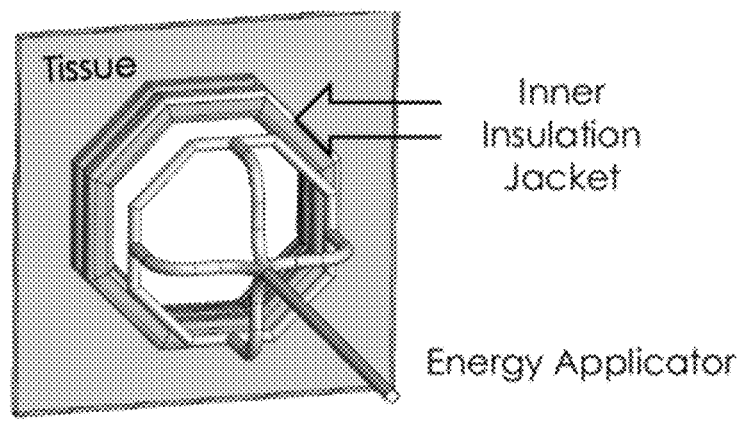
Figure 35:
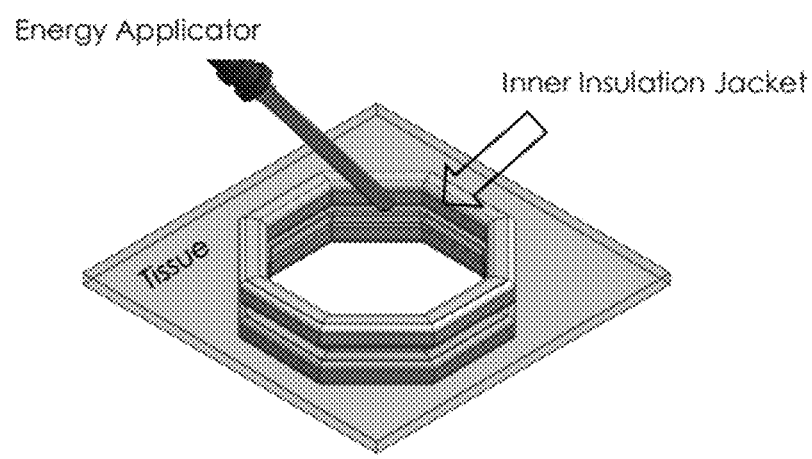

FIGS. 35(A)-35(C) schematically show compression anastomosis devices comprising an insulating jacket allowing for energy to be applied to the devices. An insulating jacket is placed inside the compression anastomosis device. After the devices mate across tissues (FIG. 35(A)), an energy applicator may be used to create a central otomy (FIGS. 35(B) and 35(C)). The compression anastomosis devices hold the tissue in place so that the devices do not shift as cautery is applied. Utilizing an energy applicator to create a central otomy allows for immediate nutrient and fluid passage through the anastomosis.

It should be noted that self-assembling magnetic anastomosis addresses several of the historical disadvantages of traditional anastomosis such as allowing a surgical-quality anastomosis in a minimally-invasive fashion using devices that reproducibly re-assemble into a larger magnet structure of a predetermined shape in vivo. The constraints imposed by the described embodiments are designed to allow the devices to consistently self-assemble into the correct shape upon deployment, which greatly reduces the risks of surgical complications due to misshapen devices or premature detachment and also reduces the risks associated with surgical access and ensure that the anastomosis is formed with the correct geometric attributes. Overall, this ensures the patency of the anastomosis.

Thus, as described herein, embodiments include flexible linear magnetic devices comprising linked magnetic multipole segments that, when extruded from the end of a deployment channel or lumen, self-assemble to form a rigid, multipolar polygonal ring magnet (PRM; generally "magnetic device"). The self-assembly is directed by the configuration of magnets, rollers, flex elements, and vertebra skins that is capable of returning to a pre-determined shape. Generally speaking, the physical and magnetic structure of the deployed magnetic devices is such that when two magnetic devices approach one another, there is a rapidly strengthening attractive magnetic interaction, which creates a coupling between the magnetic devices. In some instances, it is necessary to pre-align the complementary devices, however, in other instances the devices self-align by undergoing fast in-plane rotation with respect to one another, as discussed in detail below. As described in detail below, systems including the magnetic devices may include an endoscope having sensors that allow the endoscope to sense the position of a mating magnetic device or another endoscope that will deploy the mating device.

When deployed in adjacent tissues, for example adjacent organs or different regions of the same organ, the coupled magnetic devices create a compressive ring that can be surgically opened, or allowed to form an anastomosis without further intervention. When paired devices are left alone, the compressive force against the tissues collapse the vasculature and extrude fluids in the tissues, further reducing the distance between the devices and increasing the magnetic attraction. With time, the coupled devices eventually couple completely and fall away, leaving a formed anastomosis. This cascade begins when the devices approach within "capture range," whereby their mutually-attractive forces are sufficient to align the devices, trap the intervening tissue, and resist the natural pliancy of the tissues as well as the motion of the tissue under normal physiologic function.

Overall, the design specifications of the devices depend on the patient and the intended anastomosis. The design specifications may include: required capture range, desired effective inner and outer diameters of the deployed polygonal rings (e.g., as defined by the desired anastomosis size and instrument passage), thickness of the target tissue, and the inner diameter of guiding channel and the smallest radius of curvature to which the guiding channel may be bent and through which the magnets must pass. Once the design specifications are chosen, corresponding magnetic device designs can be determined, such as polygon-side-count and length, and the maximum lateral dimensions of the flexible linear magnetic structure that will be deployed through the delivery instrument.

Figure 1:
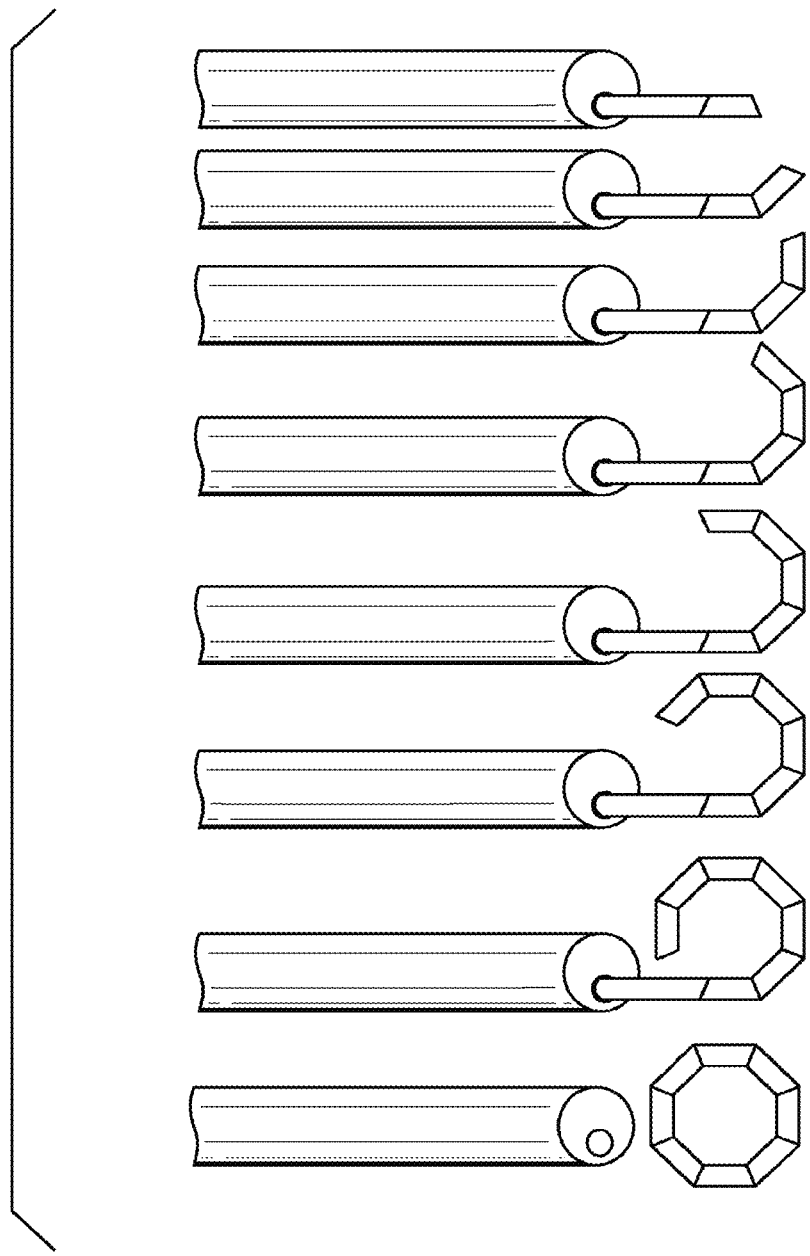
FIG. 1 shows a magnet assembly delivered through an endoscope instrument channel such that the individual magnets self-assemble into a larger magnetic structure—in this particular case, an octagon.

Deployment of a device 100 is generally illustrated in FIG. 1. When used with the techniques described herein, the devices allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. Because the magnetic devices are generally radiopaque and echogenic, the devices generally can be positioned using fluoroscopy, direct visualization (trans-illumination or tissue indentation), and ultrasound, e.g., endoscopic ultrasound. The devices can also be ornamented with radiopaque paint or other markers to help identify the polarity of the devices during placement. In some embodiments, the devices can be positioned by use of sensors located in proximity to the delivery lumen and able to sense the position of a mating device, e.g., using a Reed switch or a Hall-effect sensor.

Figure 2A:
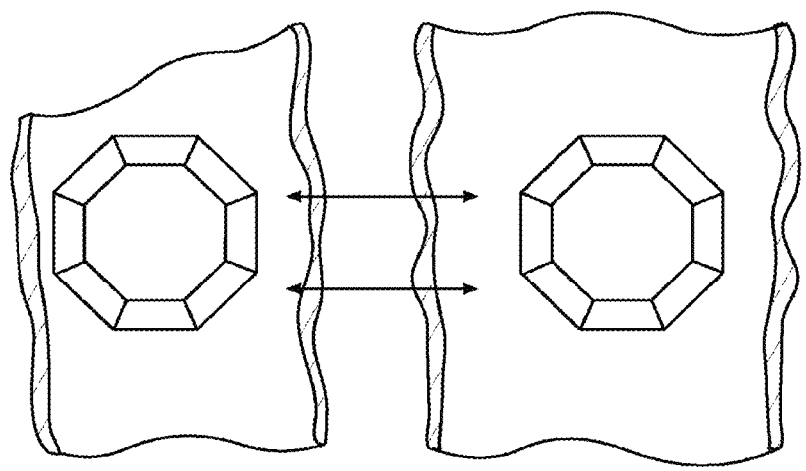
FIG. 2A shows magnet assemblies that have been delivered and deployed to adjacent tissues.
Figure 2B:
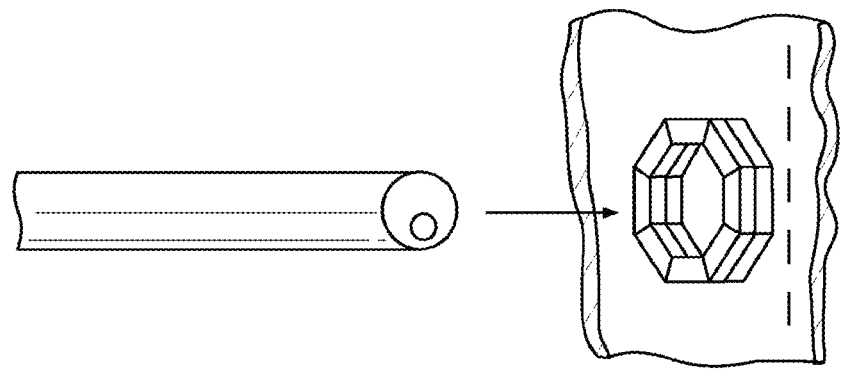
FIG. 2B shows the two magnet assemblies coupled together by magnetic attraction, capturing the intervening tissue. In some instances, the endoscope can be used to cut through the circumscribed tissue.

In general, as shown in FIG. 2A, a magnetic anastomosis procedure involves placing a first and a second magnetic structure adjacent to targeted tissues, thus causing the tissues to come together. The magnetic devices are generally deployed so that that opposite poles of the magnets will attract and bring the tissues together. The two devices may both be deployed inside the body, or one may be deployed inside the body and the other outside the body. Once the magnets have been deployed, the tissues circumscribed by the magnetic structures can be cut to provide an immediate anastomosis, as shown in FIG. 2B. In other embodiments, the tissues circumscribed by the devices will be allowed to necrose and degrade, providing an opening between the tissues. While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier.

As described with respect to the figures, a self-assembling magnetic anastomosis device can be placed with a number of techniques, such as endoscopy, laparoscopy, or with a catheter (e.g., not with direct visualization, fluoro, etc.). Regardless of method of device delivery, it is important to note that the procedure for creating the anastomosis can be terminated without perforation of tissue after confirmation of magnet coupling. As described previously, the compression anastomosis process can be allowed to proceed over the ensuing days, resulting in the natural formation of an opening between the tissues. The fused magnets can either be allowed to expel naturally or the magnets can be retrieved in a follow-up surgical procedure. Alternatively, if immediate bypass is required, the tissues circumscribed by the magnets can be cut or perforated. Perforation can be accomplished with a variety of techniques, such as cautery, microscalpel, or balloon dilation of tissue following needle and guidewire access.

Figure 3:
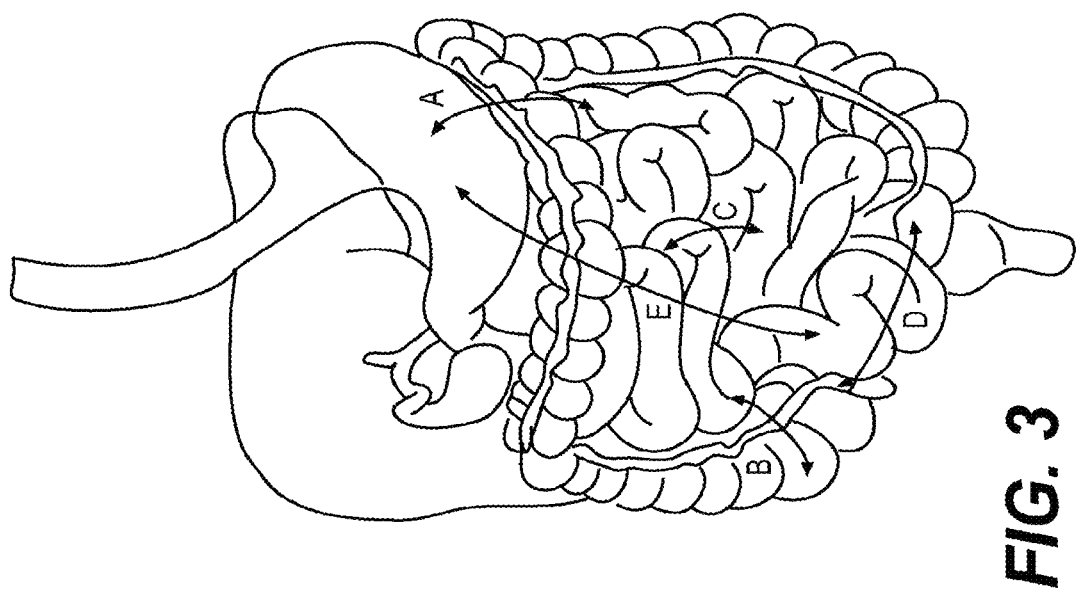
FIG. 3 shows several potential anatomical targets for anastomosis formation: Arrow A is stomach to small intestine, Arrow B is small intestine to large intestine, Arrow C is small intestine to small intestine, Arrow D is large intestine to large intestine, and Arrow E is stomach to large intestine.
Figure 4A:
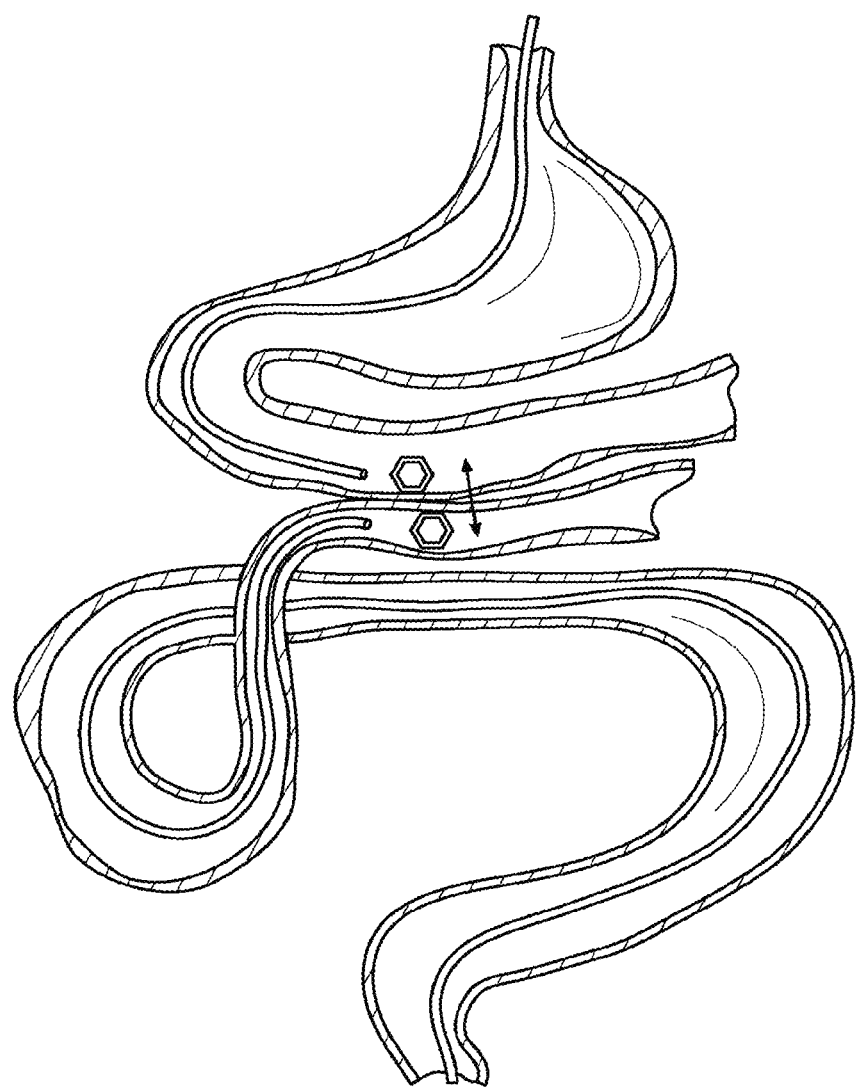
FIG. 4A shows one embodiment of delivery using two endoscopes (colonoscope and enteroscope or gastroscope) to deliver magnet assemblies.
Figure 4B:
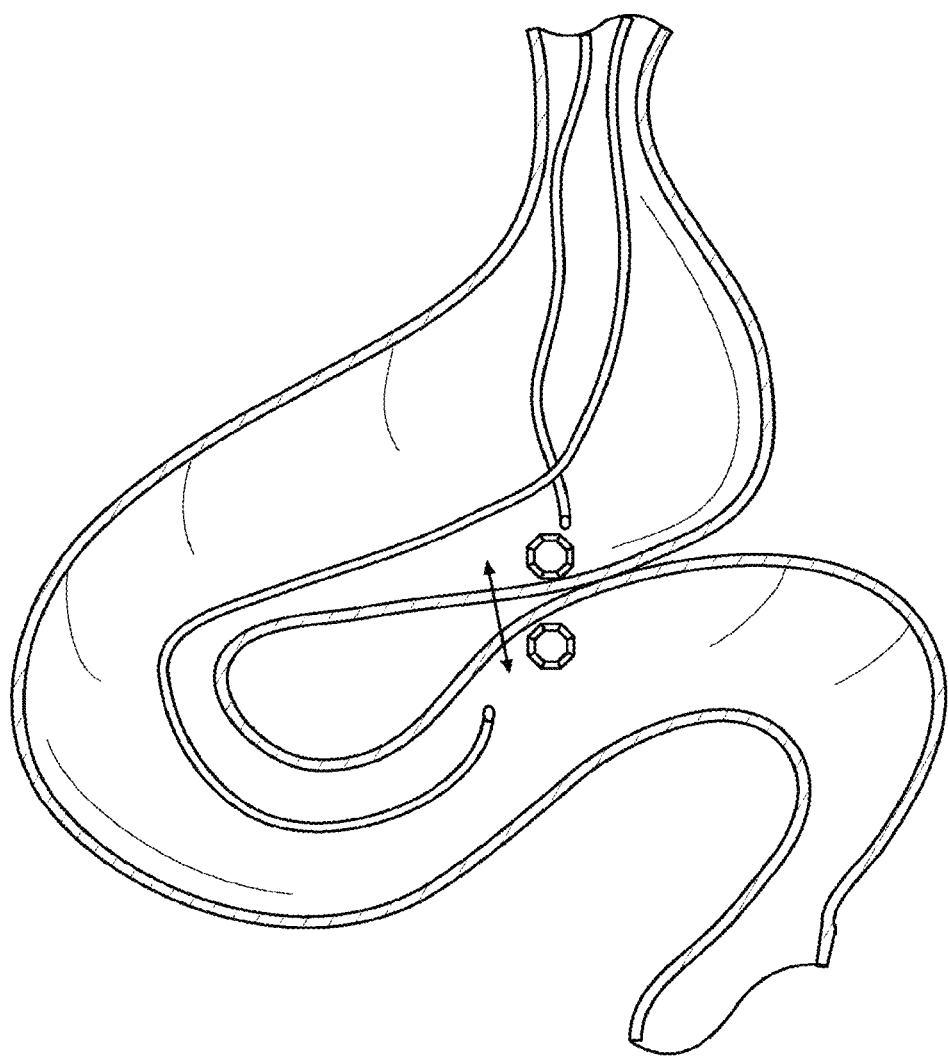
FIG. 4B shows another embodiment of delivery using two upper endoscopes both sharing per-oral entry to deliver magnet assemblies.
Figure 5:
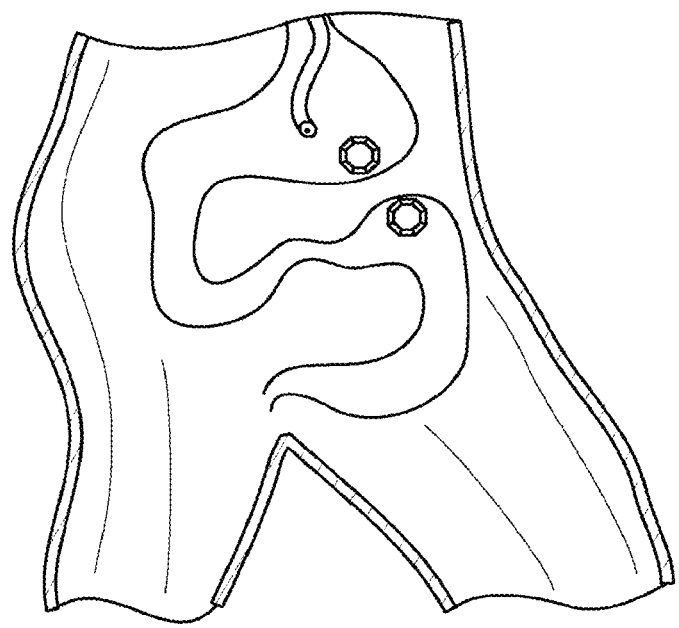
FIG. 5 shows another embodiment of delivery using a single endoscope to sequentially deliver magnet assemblies.

In some embodiments, the self-assembling magnetic devices are used to create a bypass in the gastrointestinal tract. Such bypasses can be used for the treatment of a cancerous obstruction, weight loss or bariatrics, or even treatment of diabetes and metabolic disease (i.e. metabolic surgery). Such a bypass could be created endoscopically, laparoscopically, or a combination of both. FIG. 3 illustrates the variety of gastrointestinal anastomotic targets that may be addressed with the devices of the invention: stomach to small intestine (A), stomach to large intestine (E), small intestine to small intestine (C), small intestine to large intestine (B), and large intestine to large intestine (D). In an endoscopic procedure, the self-assembling magnetic devices can be delivered using two simultaneous endoscopes, e.g., an upper endoscope or enteroscope residing in the upper small intestine, and a colonoscope residing in the lower small intestine, as shown in FIG. 4A. Alternatively, as shown in FIG. 4B, two simultaneous upper endoscopes (e.g., one residing in the stomach and the second in the small intestine) can be used to place the devices. In other embodiments, the self-assembling magnets can be delivered sequentially through the same endoscope, which has been moved between a first deployment position and a second deployment position. For example, in FIG. 4A, a single per-oral endoscope could deliver and deploy one self-assembling magnet in the small intestine, withdraw, and then deploy the second reciprocal magnet in the stomach. Again, magnet coupling could be confirmed using fluoroscopy. FIG. 5 illustrates removal of a single endoscope after placement of two magnetic devices.

A variety of techniques can be used to detect the first deployed magnetic device to assist placement of the second mating structure. Once the first device is deployed at the desired anastomotic location, the two deployed magnetic devices need to find one another's magnetic field so that they can mate and provide the compressional force needed to prompt formation of an anastomosis. Ideally, the devices can be roughly located within several cm of one another (e.g., using ultrasound), at which point the magnets should self-capture and self-align. Where this is not possible, other techniques such as one of the following techniques can be used. A first location technique involves a direct contact method using two endoscopes. Here an endoscope's displacement in an adjacent lumen creates a displacement seen by another endoscope in the adjacent lumen. The displacement identifies a potential intersection point for an anastomosis location. For example, a magnetic deployment tool (described below) will be deflected by the presence of a deployed device on the other side of a tissue wall.

The second location technique involves trans-illumination, whereby high intensity light from one endoscope is directed at the lumen wall of the proposed anastomosis site. Using this technique, another endoscope in the adjacent lumen looks for the light, which diffuses through the lumen wall and projects onto the wall of the adjacent lumen. This light represents the potential intersection anastomosis point. A cap or lens can also be placed over the light emitting endoscope to further intensify and pinpoint the proposed intersection point. A similar technique could use radio-wave- or ultrasound-transducers and receivers to collocate the endoscope tips. In some embodiments, a system may include an endoscope having a sensor and a magnetic anastomosis device for deployment using the endoscope.

A third location technique involves magnetic sensing techniques to determine the proximity of the deployed ring magnet in the adjacent lumen. By maximizing the magnetic field being sensed, the minimum distance between the adjacent channels can be identified. The magnetic sensor can be carried on a probe inserted down the working channel of the endoscope and utilize common magnetic sensing technology such as a Hall Effect Sensor or Reed switch.

With trans-illumination and magnetic sensing, an additional accessory may also assist with delivering magnetic devises to a precise anastomosis site. A radially expanding ring structure can be deployed with the endoscope or laparoscope that can press fit and seat itself on the scope's outer diameter. The outer diameter of this expanding element is sized to allow the deployed device to seat itself on this expanding element (again likely a press fit). With this expanding element and magnetic device radially seated about the endoscope axis, the endoscope can be directed to the ideal anastomotic location through direct contact, trans-illumination, or magnetic sensing, and then the mating magnet device released when the anastomosis site is identified.

Figure 6:
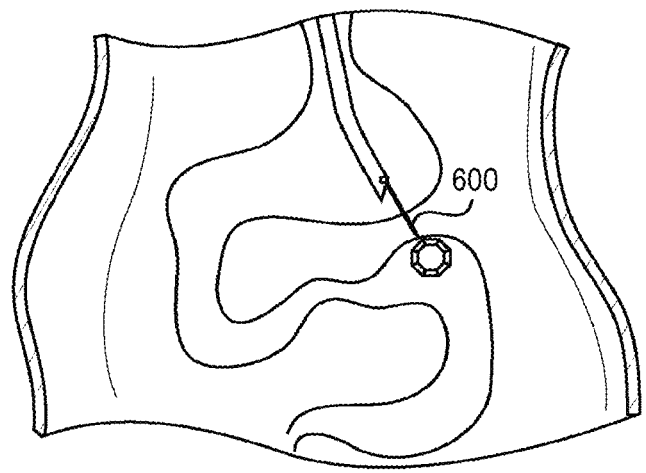
FIG. 6 shows another embodiment of delivery using endoscopic ultrasound guided needle delivery of one magnet assembly into lumen #1 followed by deployment to of the second magnet assembly in lumen #2.

In other embodiments, the self-assembling magnet devices could be delivered using ultrasound guidance, e.g., endoscopic ultrasound. For example, using an echoendoscope in the stomach, a suitable small intestine target could be identified. As shown in FIG. 6, a delivery needle 600 (e.g., an aspiration needle) or catheter can be used to access to the small intestine target and deliver the self-assembling magnets into the small intestine lumen. The delivery can be guided with fluoroscopy or endoscopic ultrasound. Following self-assembly, these small intestine magnets would couple with a second set of magnets deployed in the stomach. The two devices can be delivered with the same needle or with different needles. It is also possible to deliver the first device with an endoscope and the second device with a needle or vice versa.

Figure 7:
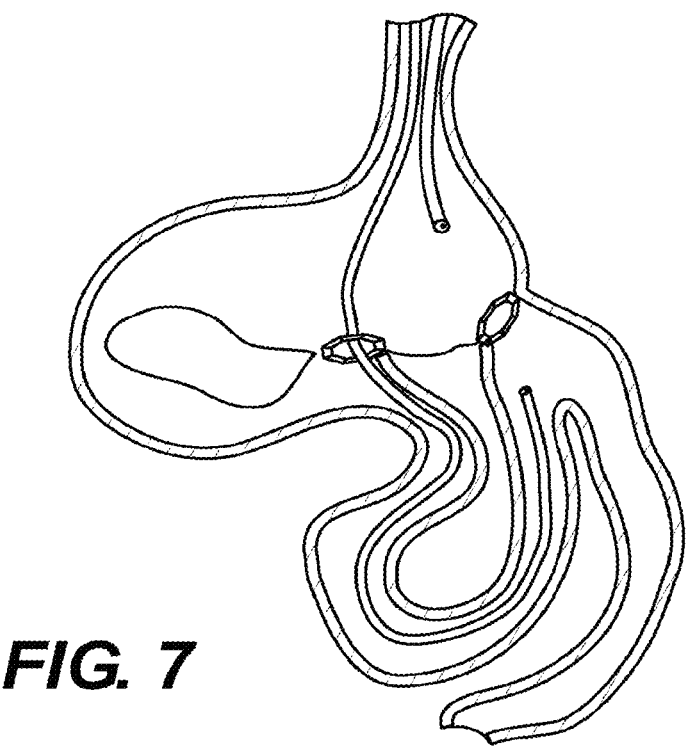
FIG. 7 shows the creation of a preliminary anastomosis to serve as a conduit for deeper endoscope delivery in order to create subsequent multiple anastomoses.

In another embodiment, illustrated in FIG. 7, a first anastomosis, created in an initial procedure, can be used to provide access for the creation of a second anastomosis. This process could theoretically be repeated multiple times to create additional anastomoses. For example, a gastrojejunal anastomosis (stomach to mid-small intestine) could serve as a conduit for the creation of a second, more distal gastrojejunal anastomosis. Ultimately, in this particular scenario, the stomach would have several bypasses to the small intestine. Additionally, in some instances, more anastomoses could be added to "titrate" to a specific clinical effect (e.g., lower glycosylated hemoglobin in type 2 diabetes). In alternative embodiments, an anastomosis may be placed to give access for a different type of surgery, e.g., tumor removal.

Figure 8:
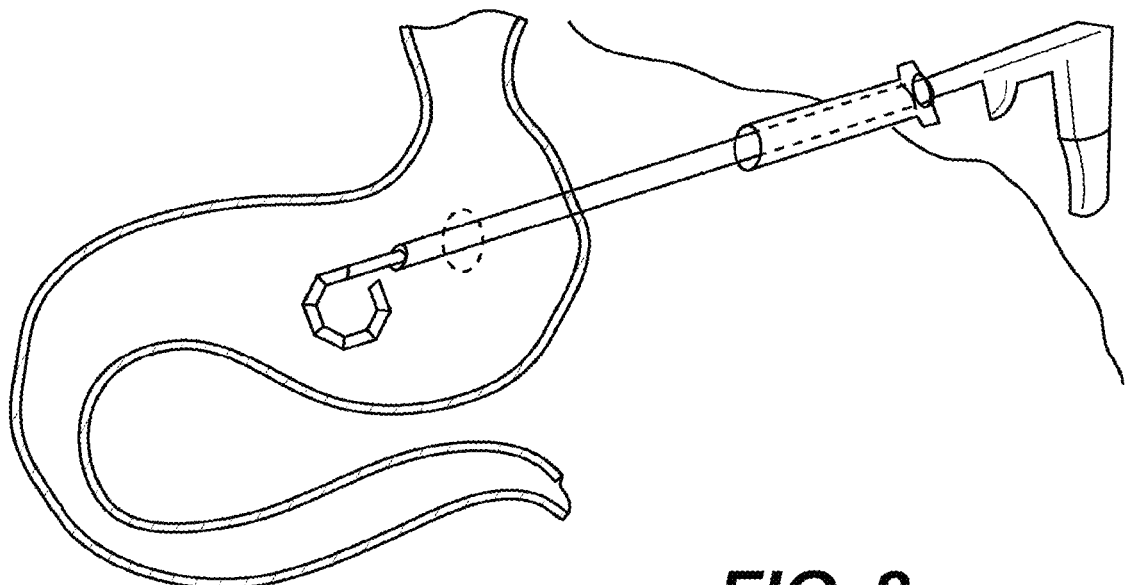
FIG. 8 shows laparoscopic magnet device delivery into a lumen (stomach, in this example).

In another embodiment of delivery, the self-assembling magnets could be delivered laparoscopically through a surgical incision into the target organs (e.g., stomach and small intestine) and allowed to couple to create an anastomosis, as shown in FIG. 8. Again, this procedure could be directed with fluoroscopy or ultrasound and the procedure can be purely laparoscopic, or a combination of endoscopic and/or laparoscopic and/or needle procedures.

Gastrointestinal anastomoses can be used to address a number of conditions. An anastomosis or series of anastomoses between the proximal bowel and distal bowel may be used for treatment of obesity and metabolic conditions, such as Type II diabetes and dyslipidemia. The procedure can also be used to induce weight loss and to improve metabolic profiles, e.g., lipid profiles. The bowel includes any segment of the alimentary canal extending from the pyloric sphincter of the stomach to the anus. In some embodiments, an anastomosis is formed to bypass diseased, mal-formed, or dysfunctional tissues. In some embodiments, an anastomosis is formed to alter the "normal" digestive process in an effort to diminish or prevent other diseases, such as diabetes, hypertension, autoimmune, or musculoskeletal disease.

Using the self-assembling magnetic devices as discussed herein, it is possible to create a side-to-side anastomosis that does not require exclusion of the intermediate tissues, as is common with state-of-the-art bariatric procedures. That is, using the devices of the invention (or other means for creating an anastomosis) it is possible to create an alternate pathway that is a partial bypass for fluids (e.g., gastric fluids) and nutrients (e.g., food), while at least a portion of the old pathway is maintained. This design allows the ratio of "normal" to "modified" digestion to be tuned based upon the goals of the procedure. In other words, using the described procedure, a doctor can choose the ratio of food/fluids shunted down the new (partial) bypass versus food/fluids shunted down the old pathway. In most instances, the fraction shunted down the bypass limb will drive the patient toward the desired clinical endpoint (e.g., weight loss, improvement in glycosylated hemoglobin, improvement in lipid profile, etc.) The mechanism by which the endpoints are achieved may involve early macronutrient delivery to the ileum with stimulation of L-cells and increase in GLP-1 production, for example. The mechanism may also involve loss of efficiency of nutrient absorption, especially glucose, thereby reducing blood glucose levels. At the same time, however, the fraction shunted down the old pathway protects against known metabolic complications that can be associated with bariatric surgery such as excessive weight loss, malabsorptive diarrhea, electrolyte derangements, malnutrition, etc.

To achieve a desired ratio of bypass (e.g., re-routing food and secretions to flow down the new pathway, say, 70% or 80% or 90% or 100% of the time), the size, location, and possibly number of anastomoses will be important. For example, for a gastrojejunal anastomosis, it may be critical to place the anastomosis in a dependent fashion to take advantage of the effects of gravity. Also, instead of a round anastomosis, it may be better to create a long, oval-shaped anastomosis to maximize anastomotic size. Alternatively, multiple gastrojejunal anastomoses may be used to titrate to a certain clinical endpoint (e.g., glycosylated hemoglobin in Type II diabetes). Most of the procedures described herein may be used to place one or more anastomoses, as needed, to achieve the desired clinical endpoint. For example, the two endoscope procedures illustrated in FIGS. 4A and 4B can be used to create a partial bypass of a portion of the bowel. Based upon the desired ratio of bypassed and non-bypassed nutrients, the anastomoses shown in FIGS. 4A and 4B can be made larger, e.g., greater than 1 cm in open diameter, or several smaller anastomoses can be placed to achieve the desired ratio.

The procedure is also adjustable. For example, a first anastomosis may be formed and then, based upon clinical tests performed after the procedure, one or more anastomoses can be added to improve the results of the clinical tests. Based upon later clinical results, it may be necessary to add yet another anastomosis. Alternatively, it is possible to partially reverse the condition by closing one or more anastomosis. Because the partially bypassed tissues were not removed, they can return to near normal functionality with the passage of greater amounts of nutrients, etc. The anastomoses may be closed with clips, sutures, staples, etc. In other embodiments, a plug may be placed in one or more anastomoses to limit the ratio of nutrients that traverse the "normal" pathway. Furthermore, it is possible to close an anastomosis in one location in the bowel and then place a new anastomosis at a different location. Thus, is possible to generally and tunably create partial bypasses, or a series of partial bypasses, between portions of the bowel to achieve clinical endpoints, e.g., as described in FIG. 3.

The described procedures may also be used with procedures that remove or block the bypassed tissues, as is common with bariatric procedures. For example, a gastrojejunal anastomosis may be coupled with a pyloric plug (gastric obstruction) or another closure of the pylorus (e.g., sutured closure) to shunt food completely down the new bypass. Such procedures can be used, for example, to bypass tissue that is diseased, e.g., because of cancer.

In another category of procedures, endoscopic ultrasound (EUS) can be used to facilitate guided transgastric or transduodenal access into the gallbladder for placement of a self-assembling magnetic anastomosis device. Once gallbladder access is obtained, various strategies can be employed to maintain a patent portal between the stomach and the gallbladder or the duodenum and the gallbladder. In another embodiment, gallstones can be endoscopically retrieved and fluid drained. For example, using the described methods, an anastomosis can be created between the gallbladder and the stomach. Once the gallbladder is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g., ethanolamine or ethanol).

Figure 9A:
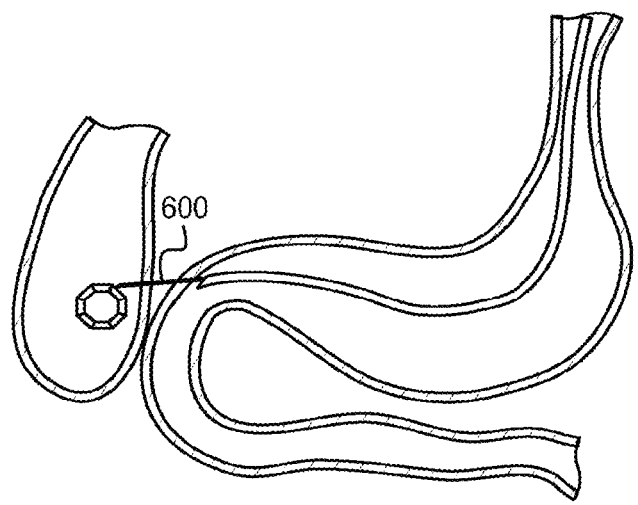
FIG. 9A shows endoscopic ultrasound guided needle delivery of a magnet assembly into the gallbladder which then couples with a second magnet assembly in the stomach or duodenum as shown in FIG. 9B.
Figure 9B:
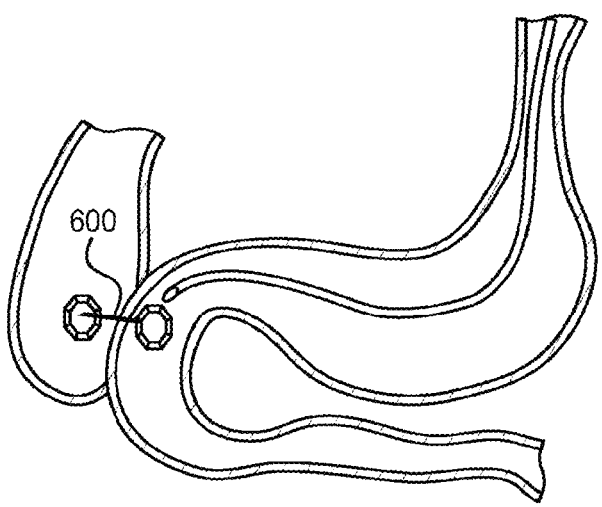

One strategy for creation of a portal is to deploy self-assembling magnets via an endoscopic needle under ultrasound guidance into the gallbladder and also into the stomach or duodenum. These magnets will mate and form a compression anastomosis or fistula. A second strategy for creation of a portal is to deploy self-assembling magnets via an endoscopic needle 600 as shown in FIGS. 9A and 9B. While the coupled magnetic assemblies are shown as octagons, the closed frame could take the shape of any polygonal structure, e.g., a square, a circle, a triangle, hexagon, heptagon, nonagon, decagon, dodecagon, etc. One such device would be deployed into the gallbladder, and the mating device would be deployed into the stomach or duodenum. In the same fashion as discussed above with respect to gastrointestinal deployment, the tissue circumscribed by the two magnetic devices can be cut with cautery, microscalpel, needle-knife, or other deployable cutting mechanism. In another embodiment, the coupled tissues can be left to necrose and form the anastomosis.

Figure 10:
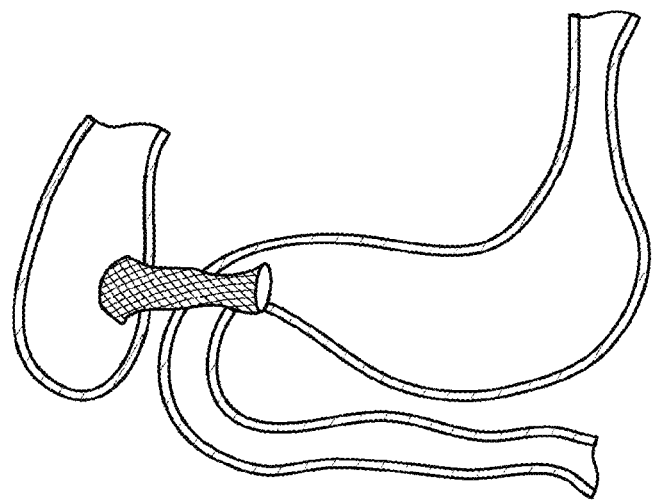
FIG. 10 shows stent deployment between the gallbladder and either the stomach or duodenum.
Figure 11:
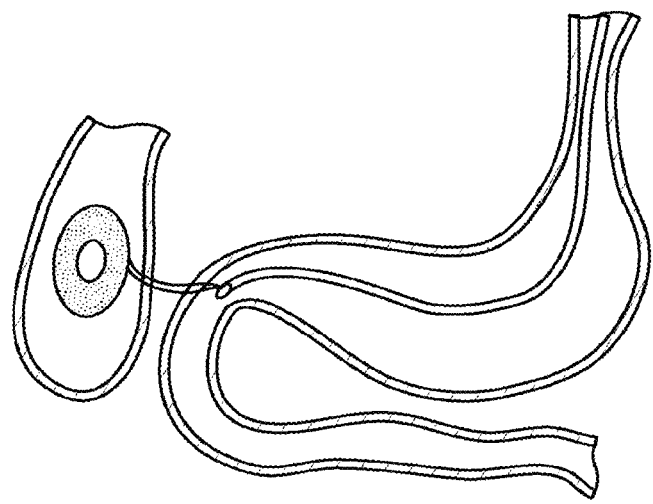
FIG. 11 shows another embodiment of an intra-gallbladder magnet assembly that is a balloon that fills with fluid, gas, or magnetic material. This balloon is tethered to the endoscope and is initially delivered through an endoscopic ultrasound guided needle.

The devices need not be limited to forming holes, however. Other structures can be coupled to one or more mating magnetic devices to created additional functionality. For example, a stent could be deployed between tissues, such as the gallbladder and the stomach, as shown in FIG. 10. Alternatively, the gallbladder magnet could be coupled to a balloon-based device that fills with air, fluid, magnetic pieces or magnetic particles. Upon inflation, the balloon would serve as an anchor in the bile duct following placement. The balloon could also have an annular configuration to allow for immediate access after coupling with the second magnet. See, e.g., FIG. 11. Regardless of embodiment, however, it is critical to contain the original access pathway within the confines of the coupled magnets, i.e., not leaving a pathway for the escape of bile. Otherwise, the opening will allow bile leakage that can result in peritonitis.

Another medical application for self-assembling magnets is direct biliary access. Currently, to achieve decompression for a malignant biliary stricture, endoscopic retrograde cholangiopancreatography (ERCP) is performed. The biliary tract is accessed endoscopically through the papilla in retrograde fashion and a stent is deployed across the stricture over a guidewire. These stents frequently require subsequent procedures for exchange, clean-out, or placement of additional overlapping stents. The need for exchange and cleaning is required to counteract the high rate of infection of the biliary tree (i.e. cholangitis) when using an ERCP procedure. Because of the high rate of morbidity, ERCP is typically limited to patients that have no other option to address pancreatic disease.

Using devices of the invention, however, it is possible to easily form an anastomosis between the bile duct (preferably the main bile duct) and either the duodenum or the stomach (choledocho-gastric and choledocho-duodenal anastomoses, respectively). This anastomosis is permanent and typically does not require intervention if located apart from the diseased tissue. In an embodiment, a biliary magnetic device is delivered directly into the bile duct under endoscopic ultrasound guidance. As described below, the self-assembling magnetic device is extruded through a needle or catheter, whereupon it deploys in the correct configuration. Using fluoroscopy or ultrasound, it is then possible to confirm that the device has self-assembled and is in the correct location. In some embodiments, the magnetic device may be tethered to the delivery needle or catheter by means of a detachable wire or suture to enable mechanical retraction until optimal positioning is confirmed.

Figure 12:
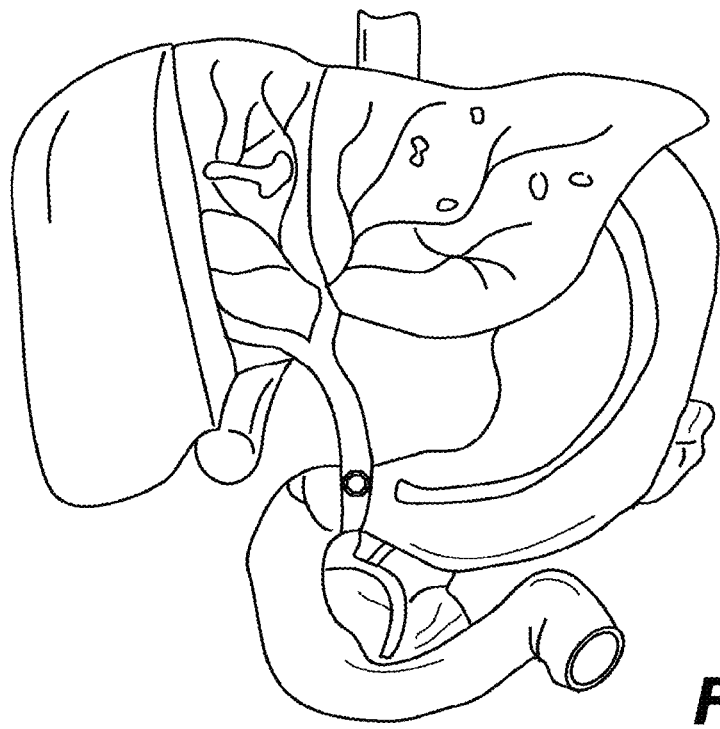
FIG. 12 shows endoscopic ultrasound guided needle delivery of a magnet assembly into the bile duct.
Figure 13:
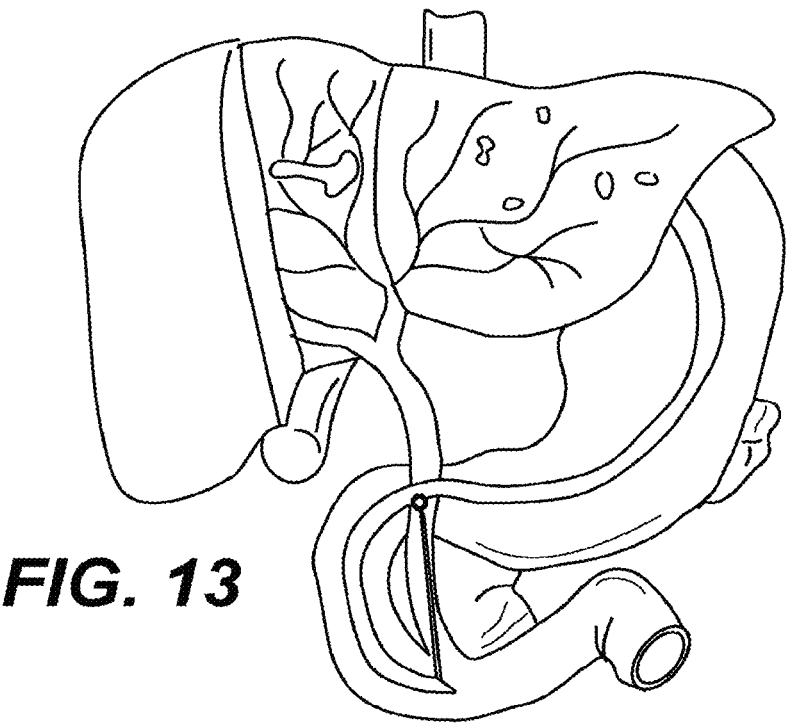
FIG. 13 shows magnet assembly delivery into the bile duct through endoscopic retrograde cholangiopancreatography techniques.
Figure 14:
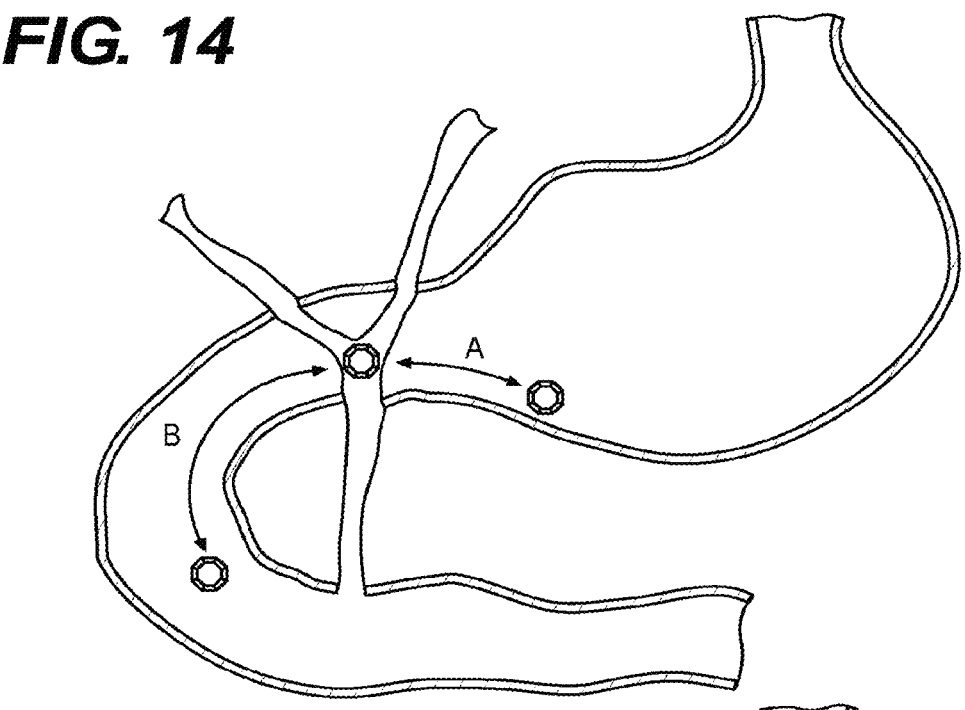
FIG. 14 shows coupling of the intra-bile duct magnet assembly with a second magnet assembly deployed either in the stomach (A) or duodenum (B).

In one embodiment, the magnetic device can be delivered endoscopically to the bile duct via wall of the duodenum, as shown in FIG. 12. In another embodiment, the biliary magnet can be delivered in conventional retrograde fashion through the ampulla into the bile duct, as shown in FIG. 13. One benefit of retrograde delivery is that it avoids needle punctures across tissue planes, as is the case with the deployment method shown in FIG. 12. Regardless of the method for delivering the biliary magnets, however, a second magnetic device is required in either the gastric (A) or duodenal (B) lumen, as shown in FIG. 14. Typically, this decision is dependent upon the patient's anatomy (e.g., size of the duodenal lumen) and the location of the initial biliary magnet. In scenarios based on endoscopic ultrasound needle delivery, the second magnetic device can be connected to the biliary magnet via the aforementioned detachable wire, and therefore extruded through the same delivery needle/catheter. Alternatively, the second device can be pre-attached to the exterior of the endoscope and slid into position for coupling after biliary magnet deployment. The latter procedure may be more applicable to forward-viewing echoendoscopes but may be used with endoscopes, generally.

Figure 15:
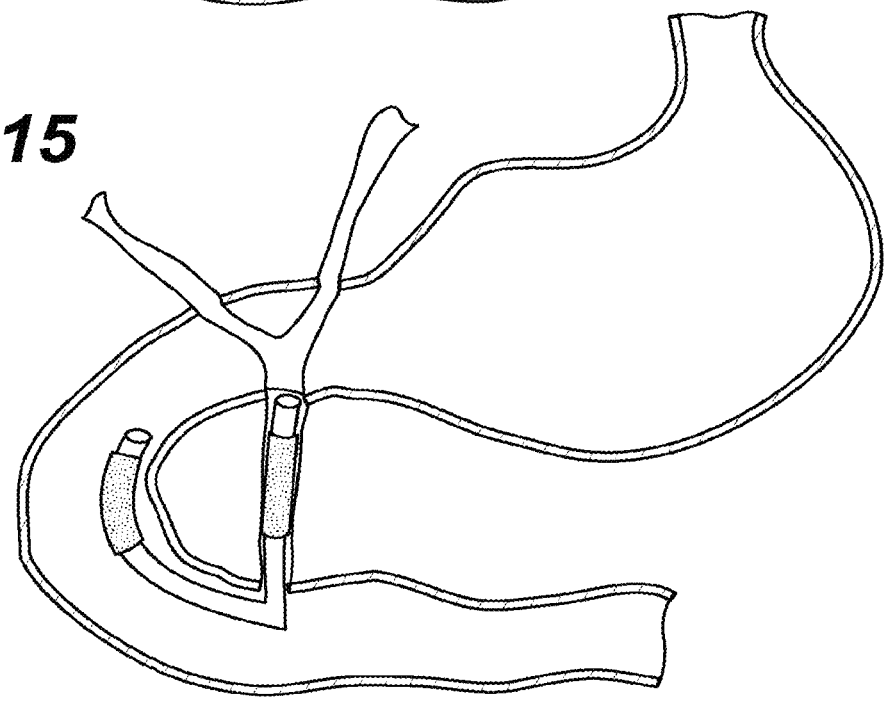
FIG. 15 shows another embodiment of bile duct magnetic anastomosis in which a hinged magnetic bile duct stent swings back onto itself by magnetic attraction to form an anastomosis between the bile duct and duodenum.

In another embodiment, the biliary magnet is a balloon-based device that fills with air, fluid, magnetic pieces or magnetic particles, similar to previously described with respect to gallbladder procedures. Upon inflation, the balloon would serve as an anchor in the bile duct following placement. In an embodiment, the balloon could have an annular configuration to allow for immediate access after coupling with the second magnet. Additionally, like the gallbladder procedures described above, a biliary magnetic device can be used with a stent form-factor. In an embodiment, the stent has an internal biliary magnet and a hinged external magnet. The stent can be inserted in retrograde fashion through the ampulla into the bile duct. The hinged external magnet can then be swung around and coupled with the internal biliary magnet to form a fistula between the bile duct and the duodenum, as shown in FIG. 15.

Figure 16:
FIG. 16 shows a magnetic stent that can be delivered into the pancreatic duct. The stent can be coupled with a magnet in the stomach (A) or in the duodenum (B) to create a drainage anastomosis for the pancreatic duct.

The magnetic devices of the invention can also be used to treat pancreatic diseases. For example, the pancreatic duct requires decompression in certain disease states, such as chronic pancreatitis. Currently, extensive pancreatic duct decompression requires surgery (e.g., Peustow surgery in which the pancreas is filleted along the axis of the pancreatic duct and connected to a loop of small intestine for improved pancreatic drainage). As an alternative to Peustow surgery, extensive pancreatic duct decompression can be accomplished via creation of a large magnetic compression anastomosis between the pancreatic duct and either the stomach or duodenum using a magnetic pancreatic catheter, as shown in FIG. 16. The catheter can be magnetic along its entire length or only at certain intervals. The catheter can be in the form of a stent or straw. The pancreatic duct can be accessed using conventional ERCP methods (retrograde cannulation through the ampulla) or by direct needle access using endoscopic ultrasound (EUS). The magnetic pancreatic catheter can be delivered into the pancreatic duct and coupled with a second magnetic device in either the stomach or duodenum. As in the biliary scenario described above, the magnetic pancreatic catheter could be hinged to the second magnetic device.

Figure 17:
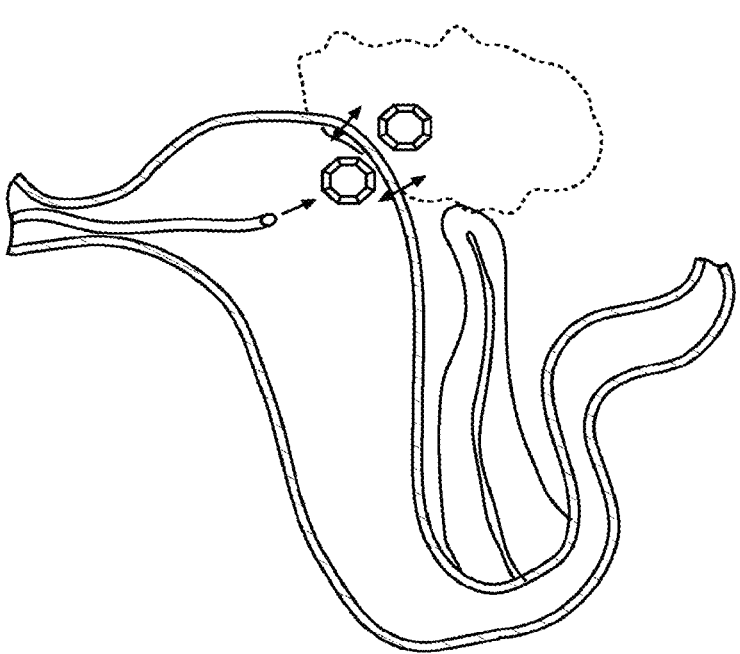
FIG. 17 shows a magnetic assembly that is delivered into a peripancreatic collection (dotted structure) using endoscopic ultrasound guided needle/catheter delivery which then couples with a second magnet assembly deployed in the stomach.

Self-assembling magnetic devices can also be used to access and drain fluid collections located adjacent to the gastrointestinal tract, as shown in FIG. 17. For example, following a bout of pancreatitis, pancreatic fluid collections can form that require drainage. While drainage can be accomplished using surgery or a percutaneous catheter, endoscopic drainage has been found to be more clinically and cost-effective, but can be complicated by bleeding, perforation, and/or inadequate drainage. As an alternative to surgical draining, magnetic devices of the invention can be delivered through a needle or sharpened catheter into the collection under endoscopic ultrasound (EUS) guidance, as shown in FIG. 17. Following assembly, the first magnetic device is coupled to the second magnetic device that has been placed in the gastrointestinal lumen (e.g. stomach). In order to speed removal after drainage, the first magnet may be tethered by a connecting wire as previously described. As described previously, the intervening tissue can be cut using electrocautery or dilation followed by needle and wire access. Additional devices, such as magnetic coupling clamps can be used to control blood flows to allow for "blood-less" endoscopic entry into the collection.

Figure 18:
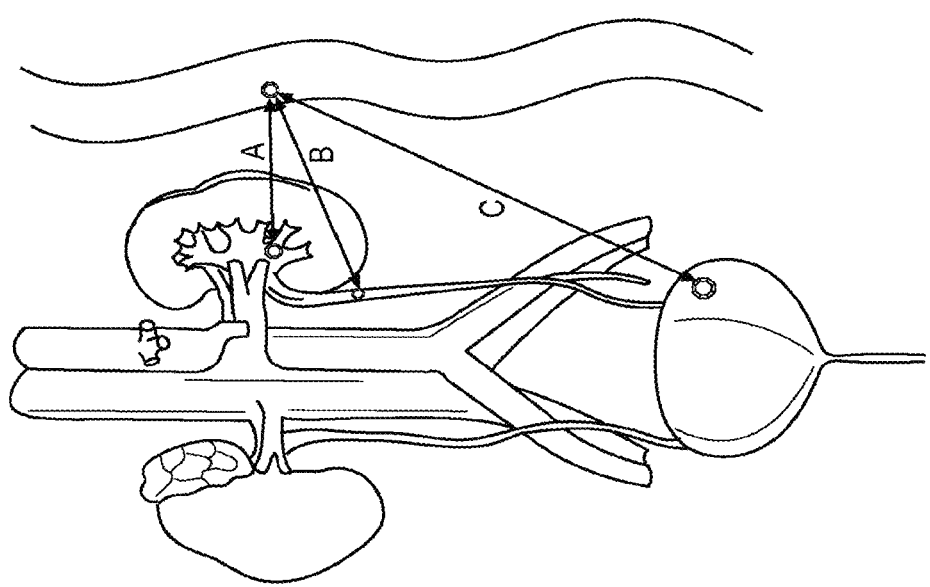
FIG. 18 shows different targets for anastomoses between the urinary system and the gastrointestinal system: renal calyx (A), ureter (B), and bladder (C).

Self-assembling magnets can also be used for urological applications such as forming bypasses to treat an obstructed urogenital tract, as shown in FIG. 18. For example, a magnetic anastomosis could be created between the renal calyx and bowel (A), between the ureter and bowel (B), or between the bladder and bowel (C). Self-assembling magnetic devices of the invention can be delivered into the urological tract using an endoscope, laparoscope, or needle, as described above. The reciprocal magnetic device could be delivered into the gastrointestinal tract using an endoscope, laparoscope, or needle as previously described. In other embodiments, the devices can be used for reproductive procedures, such as bypassing a portion of obstructed fallopian tube or bypassing a vasectomy.

Figure 19:
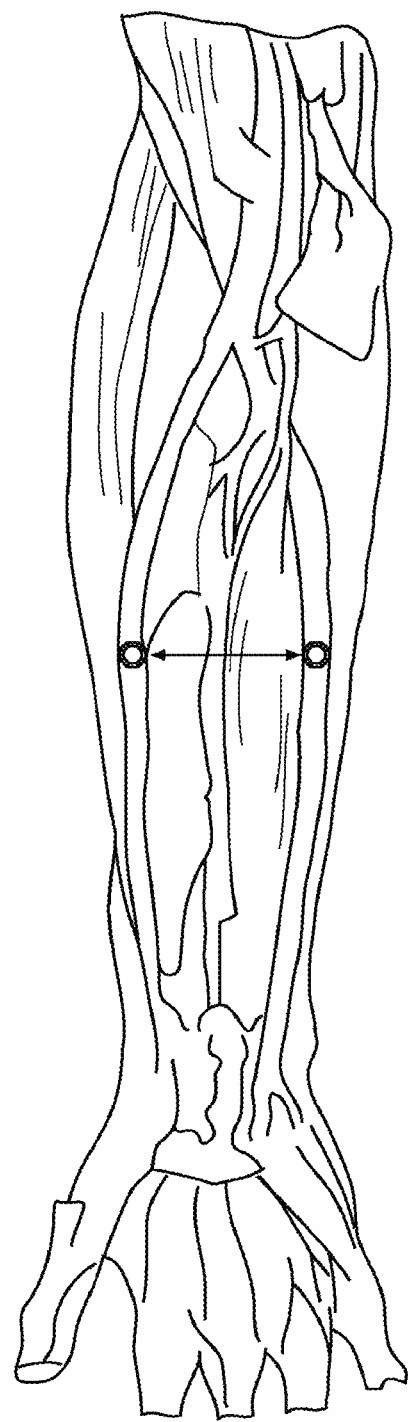
FIG. 19 shows magnet assemblies in adjacent blood vessels to couple and create a vascular anastomosis.

In yet another application, self-assembling magnetic devices can be used to create vascular anastomoses or to treat cardiac conditions. For example, a magnetic anastomosis coupling can be formed between adjacent blood vessels with magnetic devices, as shown in FIG. 19. In an embodiment, the self-assembling devices can be delivered with a vascular delivery device, such as a catheter. Additionally, as described above with respect to gallbladder and pancreatic applications, a shunt can be installed to bypass a portion of the vasculature that is weak or blocked.

Figure 20:
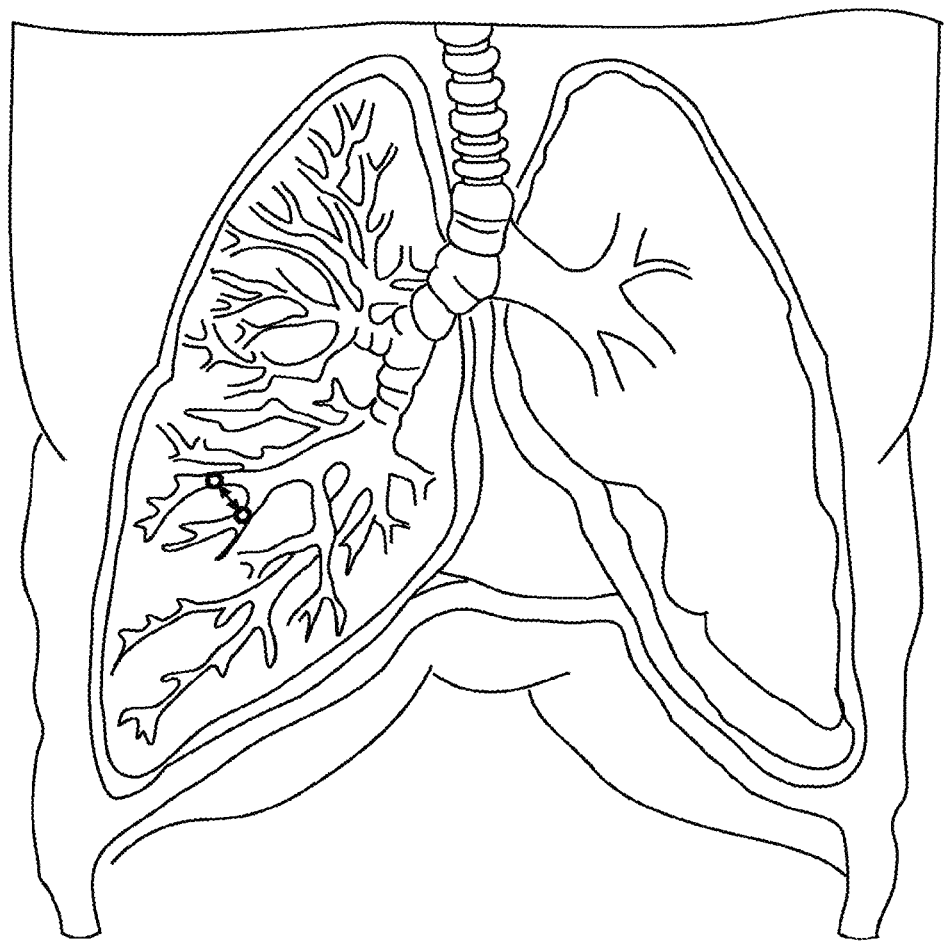
FIG. 20 shows magnet assemblies in different parts of the respiratory system to create anastomoses between adjacent bronchioles.

Self-assembling magnets can also be used for pulmonary applications such as forming bypasses in the airway to treat chronic obstructive pulmonary disease (COPD). For example, magnetic anastomoses can be created by deploying self-assembling magnetic devices into adjacent bronchioles, as shown in FIG. 20. Creation of pulmonary "bypasses" could lower airway resistance that characterizes respiratory diseases such as COPD.

Figure 21:
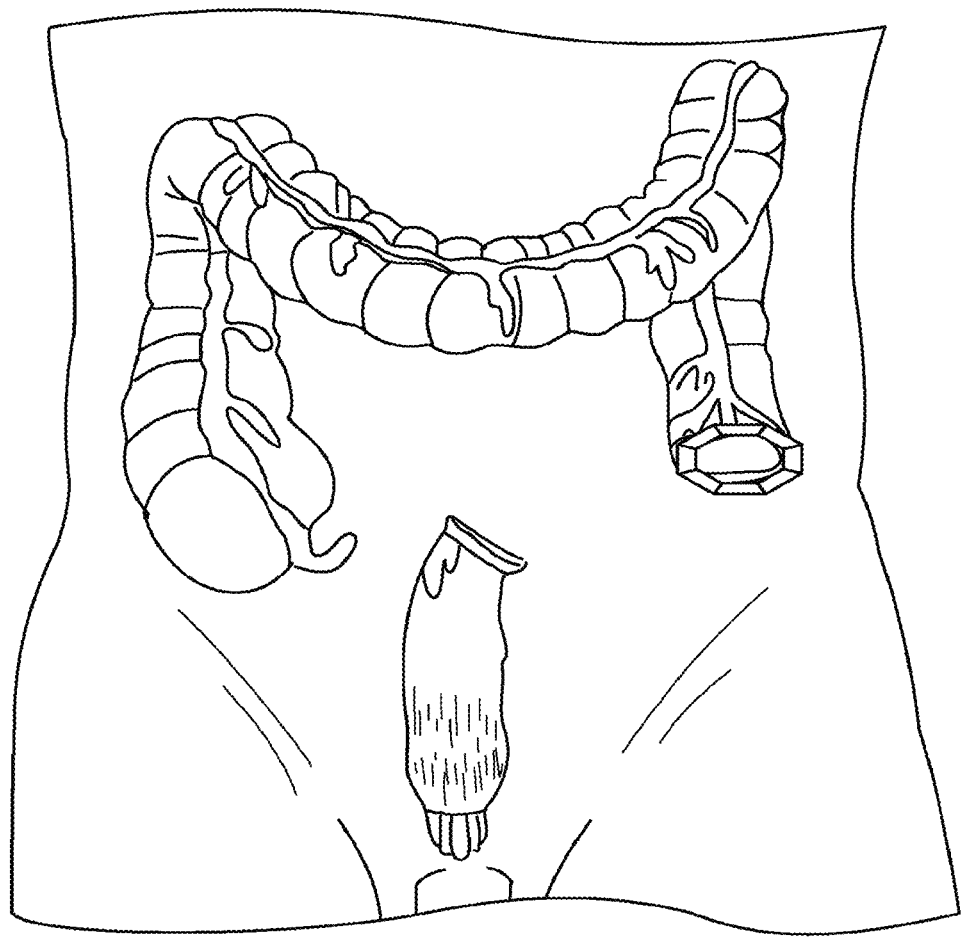
FIG. 21 shows an external magnet assembly and an internal magnet assembly within the gastrointestinal tract used to create a surgical stoma for fecal drainage.

Self-assembling magnetic devices can also be used to create surgical stomas for diversion of a fecal stream, e.g., into a colostomy bag. For example, a magnetic anastomosis can be created by deploying self-assembling magnets into the gastrointestinal tract (e.g. large intestine), as shown in FIG. 21, and then coupling the interior magnet to an external magnet worn and secured at the level of the skin. The exterior magnetic device may be coupled to yet a third magnetic device that is coupled to a collection device. Such a system allows easy removal of the collection device for cleaning, etc.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Without limitation, potential subject matter that may be claimed (prefaced with the letter "P" so as to avoid confusion with the actual claims presented below) includes:

P1. An apparatus for creating a compression anastomosis, wherein the apparatus comprises a compression anastomosis device having an annular shape and top face parallel to a diameter of the compression anastomosis device, and wherein the top face comprises one or more geometric profiles.

P2. The apparatus as described in any prior innovation, further comprising a second compression anastomosis device having an annular shape and a second top face parallel to a diameter of the second compression anastomosis device, the second top face comprising a one or more geometric profiles, wherein the one or more geometric profiles of the second top face complements the one or more geometric profiles of the first top face.

P3. The apparatus as described in any prior innovation, wherein the geometric profile is a relief profile capable of generating 0-25 psi on body tissues.

P4. The apparatus as described in any prior innovation, wherein the geometric profile is a tissue fusion profile capable of generating 25-250 psi on body tissues.

P5. The apparatus as described in any prior innovation, wherein the geometric profile is a fast release profile capable of generating 250-40,000 psi on body tissues.

P6. The apparatus as described in any prior innovation, wherein the geometric profile is a cutting profile capable of generating 40,000-75,000 psi on body tissues.

P7. The apparatus as described in any prior innovation, further comprising a plurality of connecting members arranged in an annular configuration, the plurality of connecting members comprising one or more geometric profiles.

P8. The apparatus as described in any prior innovation, further comprising a second plurality of connecting members arranged in an annular configuration, the second plurality of connecting members comprising a one or more geometric profiles, wherein the one or more geometric profiles of the second plurality of connecting members complements the one or more geometric profiles of the first plurality of connecting members.

P9. The apparatus as described in any prior innovation, wherein the geometric profile is non-uniform and non-linear.

P10. The apparatus as described in any prior innovation, wherein the geometric profile is knurled and/or cross-hatched.

P11. The apparatus as described in any prior innovation, wherein the geometric profile is an angled cutting pressure profile.

P12. The apparatus as described in any prior innovation, wherein the geometric profiles of the first plurality of connecting members and the second plurality of connecting members overlap.

P13. The apparatus as described in any prior innovation wherein the plurality of connecting members comprise one or more alternating profile zones.

P14. The apparatus as described in any prior innovation wherein the plurality of connecting members comprise two or more profile zones with one geometric shape.

P15. The apparatus as described in any prior innovation, further comprising an insulating jacket capable of allowing energy application to the apparatus.

Although the above discussion discloses various exemplary embodiments of the invention, it should be apparent that those skilled in the art can make various modifications that will achieve some of the advantages of the invention without departing from the true scope of the invention. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A magnetic compression anastomosis device comprising:
    at least one magnetic member that forms an annular shape including a tissue-engaging surface comprising a plurality of distinct pressure profile zones, where the plurality of distinct pressure profile zones comprises:
    an inner cutting zone;
    a fast release zone adjacent to the inner cutting zone;
    a tissue fusion zone adjacent to the fast release zone; and
    a relief zone adjacent to the tissue fusion zone.

2. A device according to claim 1, wherein:
    the relief zone is capable of generating pressure between around 0 psi to around 25 psi on body tissues;
    the tissue fusion zone is capable of generating between around 25 psi to around 250 psi on body tissues;
    the fast release zone is capable of generating between around 250 psi to around 40,000 psi on body tissues; and
    the cutting zone is capable of generating between around 40,000 psi to around 75,000 psi on body tissues.

3. A device according to claim 1, wherein the tissue-engaging surface comprises a knurled or cross-hatched geometric profile.

4. A device according to claim 1, wherein a geometric profile of at least one of the distinct pressure profile zones is non-uniform and non-linear.

5. A device according to claim 1, wherein the cutting zone comprises an angled cutting pressure profile.

6. A device according to claim 1, wherein the annular shape is a polygon.

7. A device according to claim 1, wherein the annular shape is a circle.

8. A device according to claim 1, wherein the at least one magnetic member comprises a plurality of magnetic members that assemble into the annular shape.

9. A device according to claim 1, wherein the at least one magnetic member is a unitary magnetic member forming the annular shape.

10. A system comprising:
    a first magnetic compression anastomosis device comprising at least one magnetic member that forms an annular shape including a tissue-engaging surface comprising a plurality of distinct pressure profile zones, wherein the plurality of distinct pressure profile zones comprises an inner cutting zone, a fast release zone adjacent to the inner cutting zone, a tissue fusion zone adjacent to the fast release zone, and a relief zone adjacent to the tissue fusion zone; and
    a second magnetic compression anastomosis device comprising at least one magnetic member that forms an annular shape including a tissue-engaging surface comprising a plurality of distinct pressure profile zones, wherein the plurality of distinct pressure profile zones comprises an inner cutting zone, a fast release zone adjacent to the inner cutting zone, a tissue fusion zone adjacent to the fast release zone, and a relief zone adjacent to the tissue fusion zone, the second magnetic compression anastomosis device and configured to engage with the first magnetic compression anastomosis device.

11. A system according to claim 10, wherein:
    the relief zone of each magnetic compression anastomosis device is capable of generating pressure between around 0 psi to around 25 psi on body tissues;
    the tissue fusion zone of each magnetic compression anastomosis device is capable of generating between around 25 psi to around 250 psi on body tissues;
    the fast release zone of each magnetic compression anastomosis device is capable of generating between around 250 psi to around 40,000 psi on body tissues; and
    the cutting zone of each magnetic compression anastomosis device is capable of generating between around 40,000 psi to around 75,000 psi on body tissues.

12. A system according to claim 10, wherein the tissue-engaging surface of at least one magnetic compression anastomosis device comprises a knurled or cross-hatched geometric profile.

13. A system according to claim 10, wherein a geometric profile of at least one of the distinct pressure profile zones of each magnetic compression anastomosis device is non-uniform and non-linear.

14. A system according to claim 10, wherein the cutting zone of each magnetic compression anastomosis device comprises an angled cutting pressure profile.

15. A system according to claim 10, wherein the annular shape of each magnetic compression anastomosis device is a polygon.

16. A system according to claim 10, wherein the annular shape of each magnetic compression anastomosis device is a circle.

17. A system according to claim 10, wherein the at least one magnetic member of each magnetic compression anastomosis device comprises a plurality of magnetic members that assemble into the annular shape.

18. A system according to claim 10, wherein the at least one magnetic member of each magnetic compression anastomosis device is a unitary magnetic member forming the annular shape.

19. A system according to claim 10, wherein the first and second devices have the same pressure profile configurations.

20. A system according to claim 10, wherein the first and second devices have different but complementary pressure profile configurations.

\* \* \* \* \*

UNITED STATES PATENT AND TRADEMARK OFFICE
CERTIFICATE OF CORRECTION

PATENT NO. : 12,070,217 B2
APPLICATION NO. : 18/241529
DATED : August 27, 2024
INVENTOR(S) : Peter F. Sugar et al.

It is certified that error appears in the above-identified patent and that said Letters Patent is hereby corrected as shown below:

In the Claims

At Column 18, Claim number 10, Line number 52, please delete "and" after "device" and before "configured"

Signed and Sealed this
First Day of October, 2024

Katherine Kelly Vidal
*Director of the United States Patent and Trademark Office*